(12) United States Patent
Ohno et al.

(10) Patent No.: US 12,042,260 B2
(45) Date of Patent: Jul. 23, 2024

(54) BIOMETRIC APPARATUS, BIOMETRIC METHOD, AND NON-TRANSITORY COMPUTER-READABLE STORAGE MEDIUM

(71) Applicant: Panasonic Intellectual Property Management Co., Ltd., Osaka (JP)

(72) Inventors: Yumiko Ohno, Osaka (JP); Kenji Narumi, Osaka (JP); Tsuguhiro Korenaga, Osaka (JP); Jin Muraoka, Kyoto (JP); Satoshi Arimoto, Shiga (JP); Takamasa Ando, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 515 days.

(21) Appl. No.: 17/316,760

(22) Filed: May 11, 2021

(65) Prior Publication Data

US 2021/0259565 A1   Aug. 26, 2021

Related U.S. Application Data

(63) Continuation of application No. PCT/JP2019/042905, filed on Oct. 31, 2019.

(30) Foreign Application Priority Data

Dec. 20, 2018 (JP) .................. 2018-238349
Oct. 3, 2019  (JP) .................. 2019-182724

(51) Int. Cl.
*A61B 5/00*   (2006.01)
*A61B 5/026*  (2006.01)
*H04N 25/76*  (2023.01)

(52) U.S. Cl.
CPC .......... *A61B 5/0261* (2013.01); *A61B 5/0082* (2013.01); *A61B 5/4064* (2013.01); *H04N 25/76* (2023.01)

(58) Field of Classification Search
CPC ... A61B 5/0261; A61B 5/0082; A61B 5/4064; H04N 25/76
See application file for complete search history.

(56) References Cited

U.S. PATENT DOCUMENTS

2014/0375785 A1\* 12/2014 Kogut .................. A61B 5/0205
                                                       600/479
2016/0373669 A1   12/2016 Ando et al.
(Continued)

FOREIGN PATENT DOCUMENTS

JP    11-164826       6/1999
JP    2017-009584    1/2017
(Continued)

OTHER PUBLICATIONS

International Search Report of PCT application No. PCT/JP2019/042905 dated Jan. 7, 2020.
(Continued)

*Primary Examiner* — Joel F Brutus
(74) *Attorney, Agent, or Firm* — Rimon P.C.

(57) ABSTRACT

A biometric apparatus includes a light source, an image sensor, a control circuit, and a signal processing circuit. The control circuit causes a light source to repeatedly emit a light pulse radiated onto a target part including a head of a target, causes an image sensor to receive a reflected light pulse which is caused as the light pulse is radiated onto the target part, causes the image sensor to output first image data indicating appearance of a face of the target, and causes the image sensor to output second image data according to distribution of an amount of light of at least one of components of the reflected light pulse. The signal processing
(Continued)

circuit generates data indicating a state of the target based on a temporal change in the first image data and a temporal change in the second image data and outputs the data.

18 Claims, 24 Drawing Sheets

(56) References Cited

U.S. PATENT DOCUMENTS

| | | | |
|---|---|---|---|
| 2017/0289468 A1* | 10/2017 | Fujii | H04N 23/74 |
| 2017/0310743 A1* | 10/2017 | Aoyama | G01R 27/04 |
| 2018/0176496 A1 | 6/2018 | Nakamura et al. | |

FOREIGN PATENT DOCUMENTS

| | | |
|---|---|---|
| JP | 2018-096988 | 6/2018 |
| WO | 2008/030542 | 3/2008 |

OTHER PUBLICATIONS

Ashit Talukder et al., "Real-time Non-Intrusive Eyetracking and Gaze-point Determination for Human-Computer Interaction and Biomedicine", SPIE Defense and Security Symposium, Optical Patter Recognition XV, Orlando, FL, Apr. 12-16, 2004.

Hirokazu Doi et al., "NIRS as a tool for assaying emotional function in the prefrontal cortex", Frontiers in Human Neuroscience, vol. 7, Article 770, Nov. 18, 2013, pp. 1-6.

Masashi Suda et al., "Decreased cortical reactivity underlies subjective daytime light sleepiness in healthy subjects: A multichannel near-infrared spectroscopy study", Neuroscience Research 60 (2008), Dec. 8, 2007, pp. 319-326.

Masashi Suda et al., "Subjective feeling of psychological fatigue is related to decreased reactivity in ventrolateral prefrontal cortex", Brain Research 1252 (2009), Dec. 6, 2008, pp. 152-160.

Mototaka Yoshioka et al., "Brain Signal Pattern of Engrossed Subjects using Near Infrared Spectroscopy (NIRS) and its Application to TV Commercial Evaluation", IJCNN, Jun. 10-15, 2012.

* cited by examiner

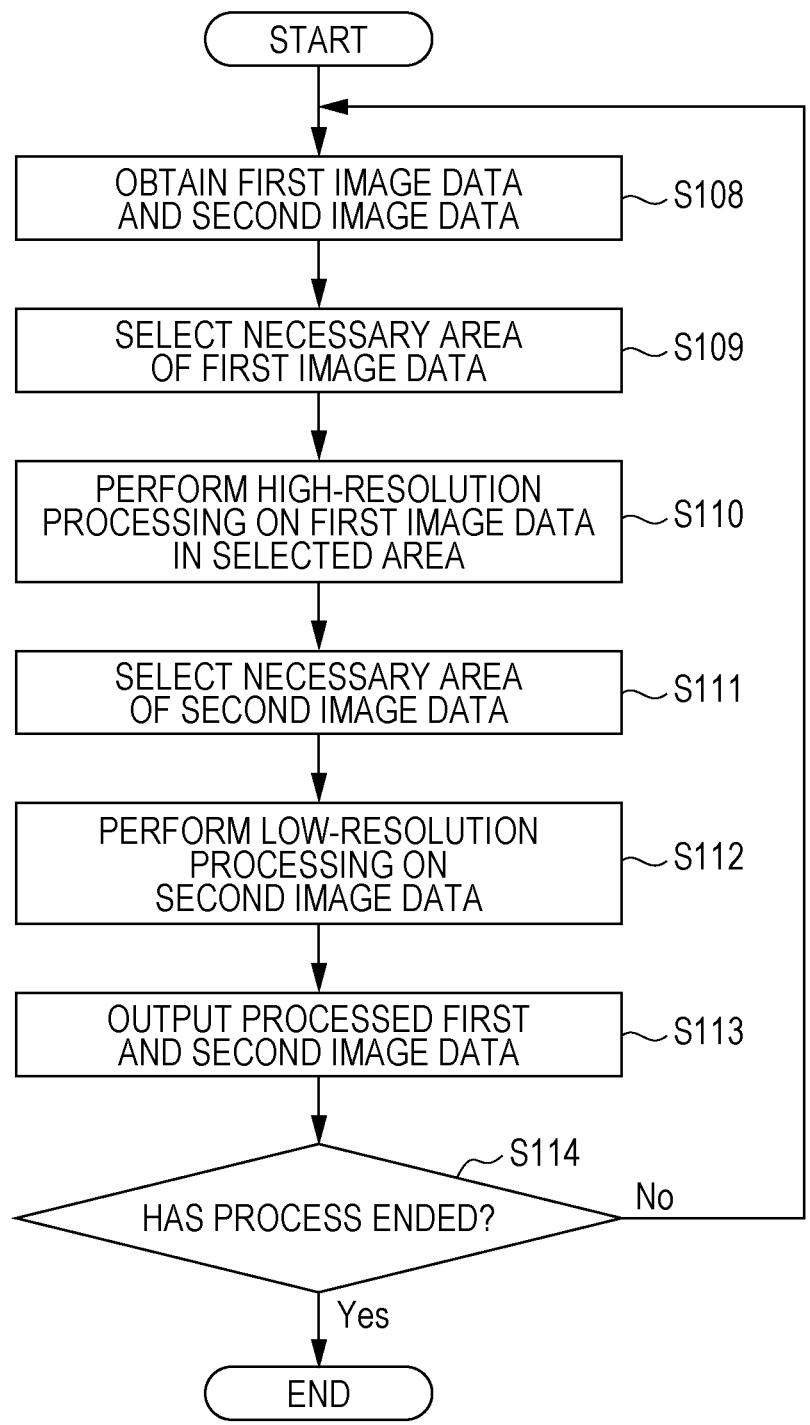

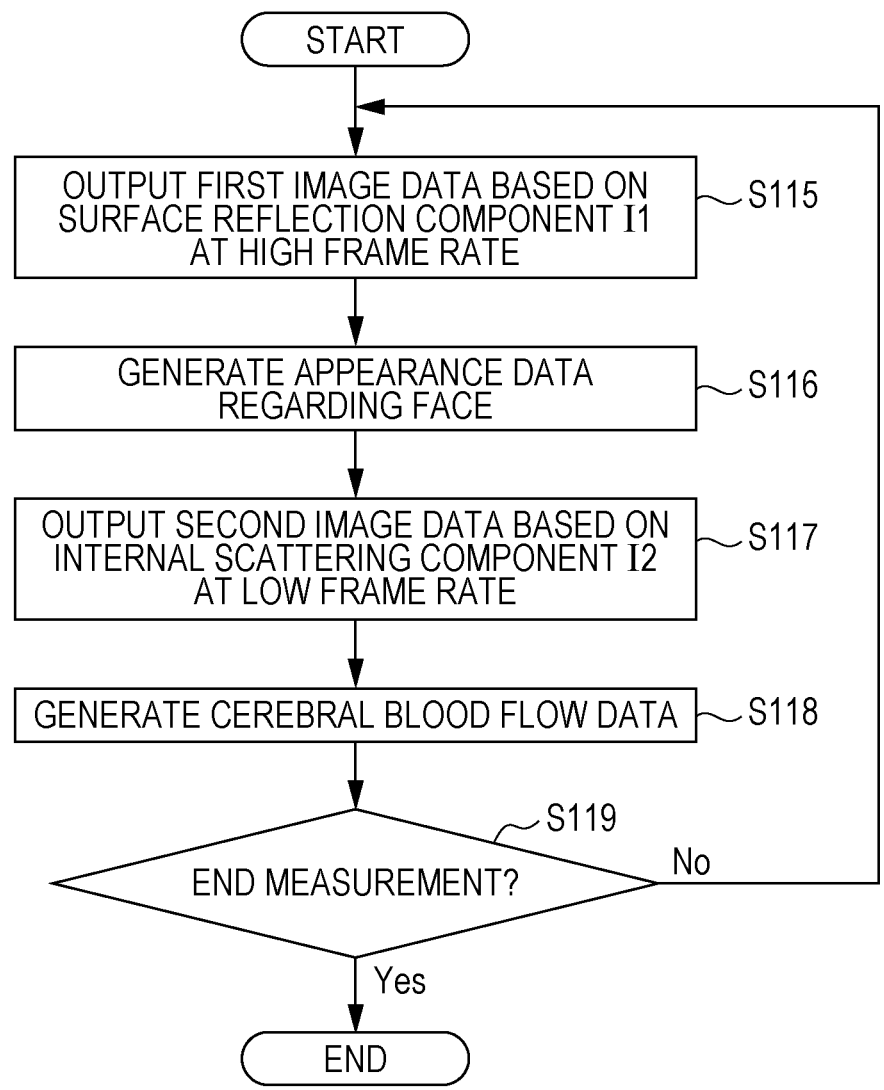

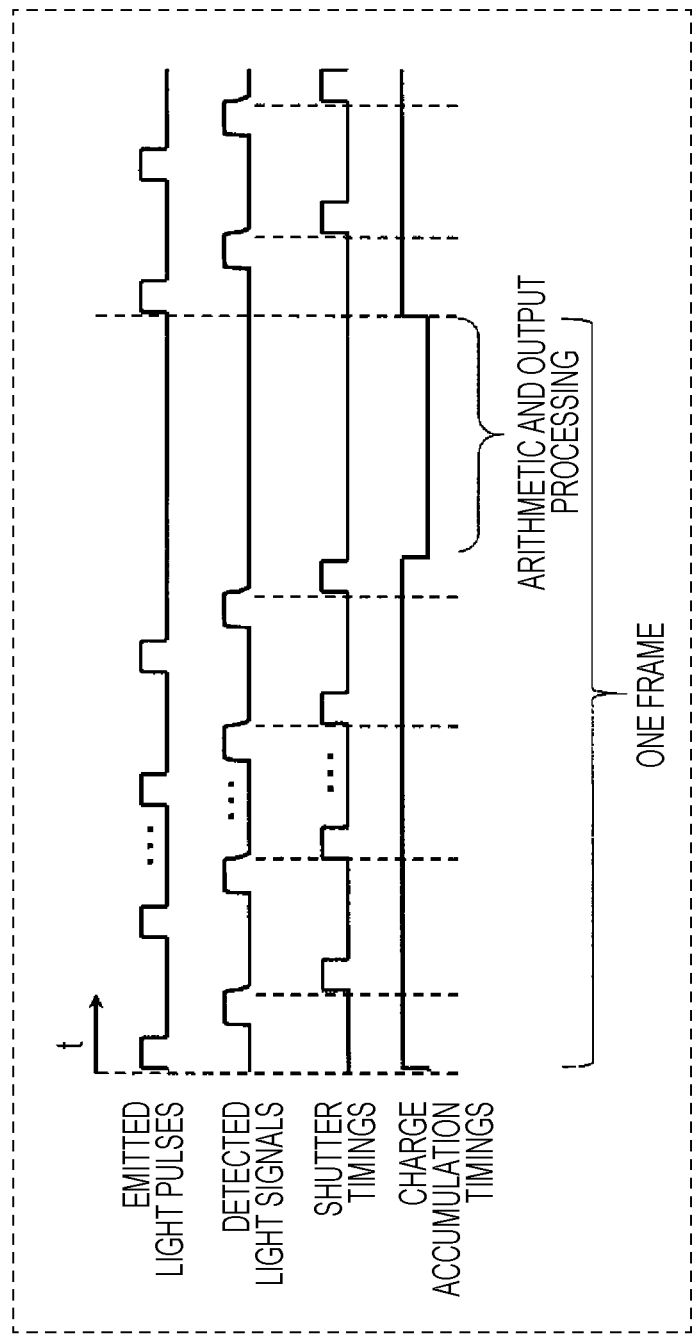

BIOMETRIC APPARATUS, BIOMETRIC METHOD, AND NON-TRANSITORY COMPUTER-READABLE STORAGE MEDIUM

BACKGROUND

1. Technical Field

The present disclosure relates to a biometric apparatus, a biometric method, and a non-transitory computer-readable storage medium.

2. Description of the Related Art

Various methods for measuring biological signals caused by brain activity of a target are known.

International Publication No. 2008/030542, for example, discloses a technique for obtaining line-of-sight data and biometric data unrelated to the eyeballs from a consumer without physically restricting the consumer while presenting a visual stimulus to the consumer and then evaluating reactions of the consumer on the basis of the line-of-sight data and the biometric data.

Japanese Unexamined Patent Application Publication No. 2017-009584 discloses an example of an imaging apparatus that obtains information indicating temporal changes in cerebral blood flow of a target in a noncontact manner.

SUMMARY

In one general aspect, the techniques disclosed here feature a biometric apparatus including a light source that emits a light pulse radiated onto a target part including a head of a target, an image sensor that receives a reflected light pulse which is caused as the light pulse is radiated onto the target part, and that outputs first image data indicating appearance of a face of the target and second image data according to distribution of an amount of light of at least one of components of the reflected light pulse, a control circuit that controls the light source and the image sensor, and a signal processing circuit. The control circuit causes the light source to emit the light pulse repeatedly and the image sensor to output the first image data and the second image data. The signal processing circuit generates data indicating a state of the target based on a temporal change in the first image data and a temporal change in the second image data and outputs the data.

It should be noted that general or specific aspects of the present disclosure may be implemented as a system, an apparatus, a method, an integrated circuit, a computer program, a computer-readable storage medium such as a storage disc, or any selective combination thereof. The computer-readable storage medium can be a nonvolatile storage medium such as a compact disc read-only memory (CD-ROM). The apparatus may be achieved by one or more apparatuses. When the apparatus is achieved by two or more apparatuses, the two or more apparatuses may be arranged in a single device or separately arranged in two or more discrete devices. An "apparatus" herein and in the claims can refer to not only a single apparatus but also a system including more than one apparatuses.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6B is a flowchart illustrating an example of a process for changing the resolution of image data obtained by a signal processing circuit from the image sensor;

FIG. 6C is a flowchart illustrating an example of a process for outputting image data while changing a frame rate using the image sensor and then generating moving image data using the signal processing circuit;

FIG. 9B is a diagram illustrating an example of a timing chart at a time when an internal scattering component is detected;

DETAILED DESCRIPTION

Figure 1A:
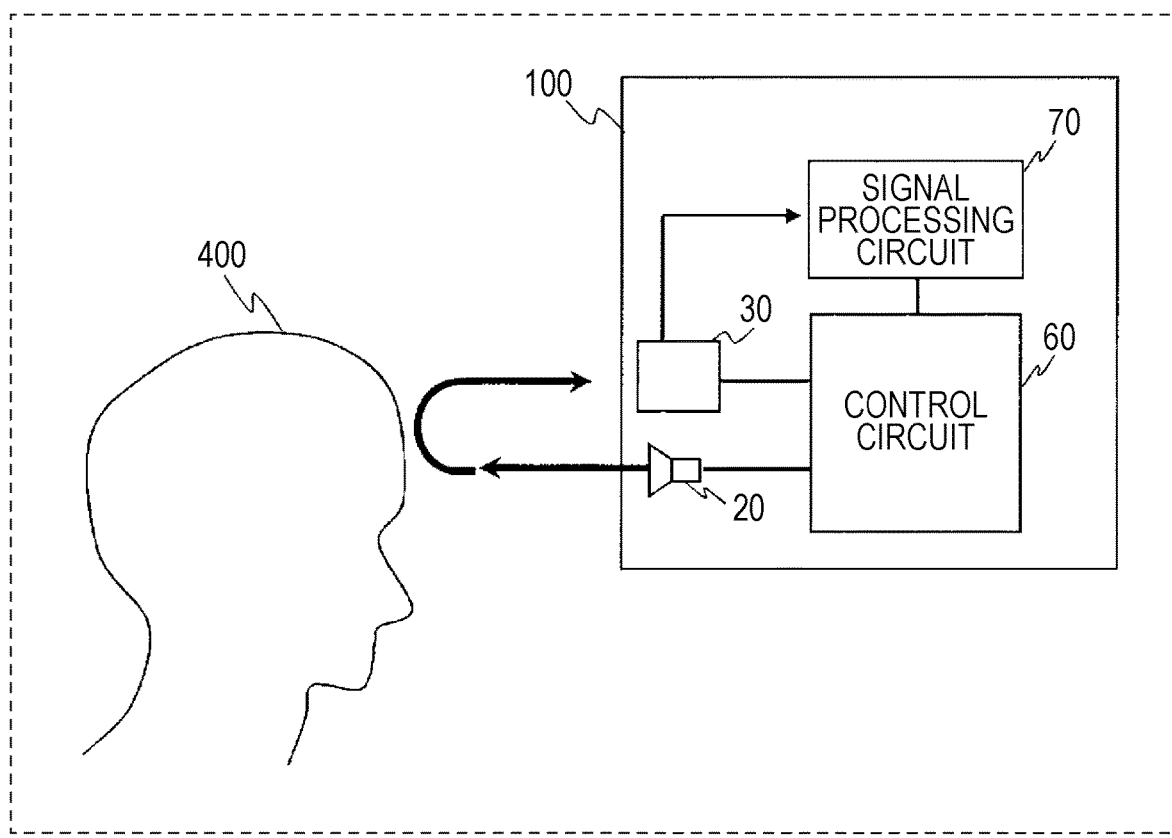
FIG. 1A is a diagram illustrating a schematic configuration of a biometric apparatus according to an exemplary embodiment of the present disclosure.

The present disclosure includes a biometric apparatus, a biometric method, a computer-readable storage medium, and a program described in the following items.

Item 1

A biometric apparatus according to Item 1 includes
a light source that emits a light pulse radiated onto a target part including a head of a target,
an image sensor that receives a reflected light pulse which is caused as the light pulse is radiated onto the target part, and that outputs first image data indicating appearance of a face of the target and second image data according to distribution of an amount of light of at least one of components of the reflected light pulse,
a control circuit that controls the light source and the image sensor, and
a signal processing circuit.
The control circuit
causes the light source to emit the light pulse repeatedly,
causes the image sensor to output the first image data, and
causes the image sensor to output the second image data, and
the signal processing circuit generates data indicating a state of the target based on a temporal change in the first image data and a temporal change in the second image data and outputs the data.

With the technique in the present disclosure, information indicating the appearance of a target's face and information indicating a state of cerebral blood flow can be obtained in a noncontact manner using a single apparatus, and a state of the target can be estimated on the basis of these piece of information.

Item 2

In the biometric apparatus according to Item 1,
the control circuit may cause the image sensor to generate the second image data by causing the image sensor to detect a component of the reflected light pulse in a period including at least a part of a falling period, the falling period being a period from a beginning to an end of a decrease in intensity of the reflected light pulse, after the falling period starts.

Item 3

In the biometric apparatus according to Item 2,
the control circuit may cause the image sensor to generate the first image data by causing the image sensor to detect a component of the reflected light pulse in a period including at least a part of a period before the falling period of the reflected light pulse starts.

Item 4

In the biometric apparatus according to any of Items 1 to 3,
resolution of the first image data and resolution of the second image data may be different from each other.

Item 5

In the biometric apparatus according to any of Items 1 to 4,
resolution of the first image data may be higher than resolution of the second image data.

Item 6

In the biometric apparatus according to any of Items 1 to 3,
the signal processing circuit may further perform a process for changing at least one resolution selected from the group consisting of resolution of at least a part of an image indicated by the first image data and resolution of at least a part of an image indicated by the second image data, and
the signal processing circuit may generate the data indicating the state of the target based on the temporal change in the first image data and the temporal change in the second image data after the process is performed.

Item 7

In the biometric apparatus according to any of Items 1 to 6,
the image sensor may output the first image data at a first frame rate,
the image sensor may output the second image data at a second frame rate, and
the first frame rate and the second frame rate may be different from each other.

Item 8

In the biometric apparatus according to any of Items 1 to 7,
the image sensor may output the first image data at a first frame rate, the image sensor may output the second image data at a second frame rate, and
the first frame rate may be higher than the second frame rate.

Item 9

In the biometric apparatus according to any of Items 1 to 8,
the image sensor may include light detection cells arranged in two dimensions,
each of the light detection cells may include a photoelectric conversion element, a first charge accumulator, and a second charge accumulator, and
the control circuit may cause the first charge accumulator to accumulate first charge,
the first image data may be generated based on the first charge,
the control circuit may cause the second charge accumulator to accumulate second charge, and
the second image data may be generated based on the second charge.

Item 10

In the biometric apparatus according to Items 1 to 9,
the signal processing circuit may detect, based on the temporal change in the first image data, a temporal change in appearance information indicating at least one selected from the group consisting of a line of sight of the target, size of a pupil of the target, frequency of blinking of the target, time intervals of blinking of the target, and facial expression of the target, and the signal processing circuit may generate the data indicating the state of the target based on the temporal change in the appearance information and the temporal change in the second image data.

Item 11

In the biometric apparatus according to any of Items 1 to 10, the control circuit may cause the light source to emit the light pulse and the image sensor to generate the first image data and the second image data with a stimulus given to the target, and the data indicating the state of the target may indicate at least one state selected from the group consisting of interest of the target, comfort of the target, sleepiness of the target, and concentration of the target in reaction to the stimulus.

Item 12

In the biometric apparatus according to any of Items 1 to 11, the signal processing circuit may present the data indicating the state of the target to the target through an information device.

Item 13

A biometric method according to Item 13 includes causing a light source to repeatedly emit a light pulse radiated onto a target part including a head of a target, causing an image sensor to receive a reflected light pulse which is caused as the light pulse is radiated onto the target part, causing the image sensor to output first image data indicating appearance of a face of the target, causing the image sensor to output second image data according to distribution of an amount of light of at least one of components of the reflected light pulse, and generating data indicating a state of the target based on a temporal change in the first image data and a temporal change in the second image data and outputting the data.

Item 14

A computer-readable storage medium according to Item 14 is a computer-readable storage medium storing a program for measuring a state of a target, the program, when executed by a computer, causing the computer to perform a process including causing a light source to repeatedly emit a light pulse radiated onto a target part including a head of a target, causing an image sensor to receive a reflected light pulse which is caused as the light pulse is radiated onto the target part, causing the image sensor to output first image data indicating appearance of a face of the target, causing the image sensor to output second image data according to distribution of an amount of light of at least one of components of the reflected light pulse, and generating data indicating the state of the target based on a temporal change in the first image data and a temporal change in the second image data and outputting the data.

Item 15

A program according to Item 15 causes a computer to perform a process including causing a light source to repeatedly emit a light pulse radiated onto a target part including a head of a target, causing an image sensor to receive a reflected light pulse which is caused as the light pulse is radiated onto the target part, causing the image sensor to output first image data indicating appearance of a face of the target, causing the image sensor to output second image data according to distribution of an amount of light of at least one of components of the reflected light pulse, and generating data indicating a state of the target based on a temporal change in the first image data and a temporal change in the second image data and outputting the data.

Embodiments described below are general or specific examples. Values, shapes, materials, components, arrangement positions and connection modes of the components, steps, and order of the steps described in the following embodiments are examples, and do not limit the techniques disclosed in the present disclosure. Among the components in the following embodiments, ones not described in the independent claims, which define broadest concepts, will be described as optional components. The drawings are schematic diagrams and not necessarily exact. Furthermore, substantially the same or similar components are given the same reference numerals in the drawings. Redundant description might be omitted or simplified.

In the present disclosure, some or all of circuits, units, apparatuses, members, or parts, or some or all of functional blocks in block diagrams, for example, can be implemented as one or more electronic circuits including a semiconductor device, a semiconductor integrated circuit (IC), a large-scale integration (LSI) circuit. The LSI circuit or the IC may be integrated on a single chip or achieved by combining chips together. Functional blocks other than storage devices, for example, may be integrated on a single chip. Although "LSI" or "IC" is used here, a term used differs depending on a degree of integration, and "system LSI", "very-large-scale integration (VLSI)", or "ultra-large-scale integration (ULSI)" may be used, instead. A field-programmable gate array (FPGA), which is programmed after an LSI circuit is fabricated, or a reconfigurable logic device, which can reconfigure connection relationships inside an LSI circuit or set up circuit sections inside an LSI circuit, can also be used for the same purposes.

Furthermore, functions or operations of some or all of the circuits, the units, the apparatuses, the members, or the parts can be performed through a software process. In this case, software is stored in one or more non-transitory storage media such as read-only memories (ROMs), optical discs, or hard disk drives, and when a processor executes the software, functions specified by the software are executed by the processor and peripheral devices. A system or an apparatus may include the one or more non-transitory storage media storing the software, the processor, and necessary hardware devices, such as an interface.

First, an example of the basic configuration of a biometric apparatus according to an embodiment of the present disclosure will be described.

FIG. 1A is a diagram illustrating a schematic configuration of a biometric apparatus 100 according to an exemplary embodiment of the present disclosure. FIG. 1A illustrates a target of biometrics, that is, a user 400 of the biometric apparatus 100.

The biometric apparatus 100 includes a light source 20, an image sensor 30, a control circuit 60, and a signal processing circuit 70. The light source 20 emits a light pulse radiated onto a target part including the target's head. The image sensor 30 receives a reflected light pulse, which is caused as the light pulse is radiated onto the target part, and outputs image data. The control circuit 60 controls the light source 20 and the image sensor 30. The signal processing circuit 70 processes the image data output from the image sensor 30. The signal processing circuit 70 then generates signals regarding brain activity of the target and outputs the signals. The control circuit 60 and the signal processing circuit 70 may be achieved by a single integrated electric circuit.

The control circuit 60 performs the following operations.
(1) Causes the light source 20 to emit a light pulse repeatedly.
(2) Causes the image sensor 30 to output first image data indicating the appearance of the target's face.
(3) Causes the image sensor 30 to output second image data according to distribution of the amount of light of some components of the reflected light pulse.

The signal processing circuit 70 generates data indicating a state of the target on the basis of temporal changes in the first image data and temporal changes in the second image data and outputs the data. As described later in detail, for example, the data indicating the state of the target reflects a psychological state or a physical state of the target. The data can indicate, for example, at least one state selected from a group consisting of interest, comfort, sleepiness, and concentration in reaction to a stimulus given to the target. The data indicating the state of the target output from the signal processing circuit 70 can be used, for example, to control another device.

With the above configuration, the biometric apparatus 100 can obtain information indicating the appearance of the target's face and information indicating the state of cerebral blood flow in a noncontact manner using a single apparatus. Furthermore, the psychological state or the physical state of the target can be estimated on the basis of the obtained information.

The first image data and the second image data are generated, for example, by the following method.

The first image data can be generated, for example, on the basis of components of a reflected light pulse in a period including at least a part of a period before a falling period of the reflected light pulse starts. A "falling period" herein refers to a period from a beginning of a decrease in a light pulse to an end of the decrease at a position of a light receiving surface of the image sensor 30. The control circuit 60 can cause the image sensor 30 to generate the first image data by causing the image sensor 30 to detect the components of the reflected light pulse in the period including at least a part of the period before the falling period of the reflected light pulse starts. The "period including at least a part of the period before the falling period of the reflected light pulse starts" may include the entirety of a period in which the reflected light pulse is incident on the image sensor 30.

The first image data can be generated on the basis of light different from the light pulse emitted from the light source 20, instead. For example, data regarding a face image captured under light from a lighting device other than the light source 20 or background light such as sunlight may be used as the first image data, instead.

The second image data can be generated, for example, on the basis of some components of the reflected light pulse included in the falling period of the reflected light pulse. The control circuit 60 can cause the image sensor 30 to generate the second image data by causing the image sensor 30 to detect the components of reflected light pulses in a period including at least a part of the falling period after the falling period starts.

As described in detail later, the intensity of components after a falling period of a reflected light pulse starts, that is, trailing edge components of the reflected light pulse, varies depending on the brain activity of the target. The psychological state or the physical state of the target can be estimated on the basis of such varying components.

With the above configuration, the first and second image data can be generated in a noncontact manner using the image sensor 30. More than one image sensors need not be provided, and the compact biometric apparatus 100 can be achieved at low cost. In addition, since only one image sensor is used, synchronization between image sensors need not be performed. In addition, when a light pulse emitted from the light source 20 is an infrared pulse, for example, signal interference that could otherwise be caused when a reflected light pulse of the infrared pulse enters other image sensors for generating a face image can be suppressed.

The image sensor 30 can be controlled in such a way as to output the first image data at a first frame rate and the second image data at a second frame rate. The first frame rate may be higher than, the same as, or lower than the second frame rate. A change in the appearance of the face is usually faster than a change in cerebral blood flow. When the first frame rate is higher than the second frame rate, therefore, more frames can be used for appearance information, which changes relatively fast. Even when the second frame rate is lower than the first frame rate, processing is not usually affected since a change in cerebral blood flow is relatively slow.

Resolution may be different between the first image data and the second image data. Data capacity can be effectively used by increasing the resolution of an image to be focused upon.

The resolution of the first image data may be higher than that of the second image data. When the resolution of the first image data is high, changes in the appearance of the face can be easily detected. The first image data may be image data in which edges are emphasized or extracted. The first image data may indicate an image in which only appearance information to be focused upon is extracted. When a line of sight or blinking is to be focused upon, for example, the first image data may indicate an image of only one eye or an image of both eyes. By limiting a part to be focused upon, the amount of data can be reduced and data processing speed can be increased. When images are captured, the target may wear a vision aid or an eyewear such as glasses or contact lenses.

The first image data can be generated on the basis of at least one of light pulses radiated onto the target part. The second image data may indicate an image of a resolution lower than that of the first image data. By decreasing the resolution of the second image data, the amount of data can be reduced and data processing speed can be increased. In order to decrease the resolution, the second image data may be smoothed using a spatial filter having a size of 50×50. As a result of the smoothing, noise included in weak cerebral blood flow signals can be reduced. Alternatively, the amount of data may be reduced by performing a process for decreasing the number of tones (i.e., the number of bits) of an image. Alternatively, the amount of data may be reduced by performing a process for spatially thinning out pixels from an image or a resizing process and —generating a low-resolution image. By decreasing the number of tones or the number of pixels, data processing speed can be increased.

The resolution of the first and second image data may be changed by the signal processing circuit 70 during signal processing or by adjusting an operation or an output of the light source 20 and/or the image sensor 30 using the control circuit 60.

The image sensor 30 can include light detection cells arranged in two dimensions. Each of the light detection cells may include a photoelectric conversion element, a first charge accumulation unit, and a second charge accumulation unit. For example, the control circuit 60 performs the following operations.

(a) Causes the light source 20 to emit a light pulse.

(b) Causes the first charge accumulation unit of at least one of the light detection cells to accumulate first charge generated when components of a reflected light pulse in a period including at least a part of a period before a falling period of the reflected light pulse starts are incident on the photoelectric conversion element.

(c) Causes the second charge accumulation unit of the at least one of the light detection cells to accumulate second charge generated when components of the reflected light pulse in a period including at least a part of a falling period of the reflected light pulse after the falling period starts are incident on the photoelectric conversion element.

(d) Causes the image sensor 30 to generate first image data on the basis of the first charge accumulated in the first charge accumulation unit of the at least one of the light detection cells.

(e) Causes the image sensor 30 to generate second image data on the basis of the second charge accumulated in the second charge accumulation unit of the at least one of the light detection cells.

The operations (a) to (c) may be repeatedly performed. In this case, in the operations (d) and (e), the image sensor 30 generates first image data of one frame on the basis of first charge repeatedly accumulated in the first charge accumulation unit and second image data of one frame on the basis of second charge repeatedly accumulated in the second charge accumulation unit.

With this configuration, the first image data and the second image data can be efficiently generated.

The signal processing circuit 70 can detect changes in the appearance of the target on the basis of temporal changes in the first image data. A known recognition algorithm, for example, may be used to detect changes in the appearance. The signal processing circuit 70 may detect temporal changes in appearance information indicating at least one item selected from a group consisting of, for example, a line of sight of the target, the size of the pupil of the target, the frequency of blinking of the target, time intervals of blinking of the target, and facial expression of the target. The signal processing circuit 70 can generate data indicating a state of the target on the basis of the temporal changes in the appearance information and temporal changes in the second image data.

The control circuit 60 may cause the light source 20 to emit light pulses and the image sensor 30 to generate the first image data and the second image data with a visual stimulus or an audio stimulus given to the target. The data indicating a state of the target may indicate at least one state selected from a group consisting of interest, comfort, sleepiness, and concentration of the target in reaction to the stimulus given to the target.

The signal processing circuit 70 or the control circuit 60 may present information determined in accordance with the state of the target to the target through an information device.

Embodiments of the present disclosure will be described more specifically hereinafter. In the following description, the same or similar components are given the same reference numerals.

Embodiments

1. Biometric System

Figure 1B:
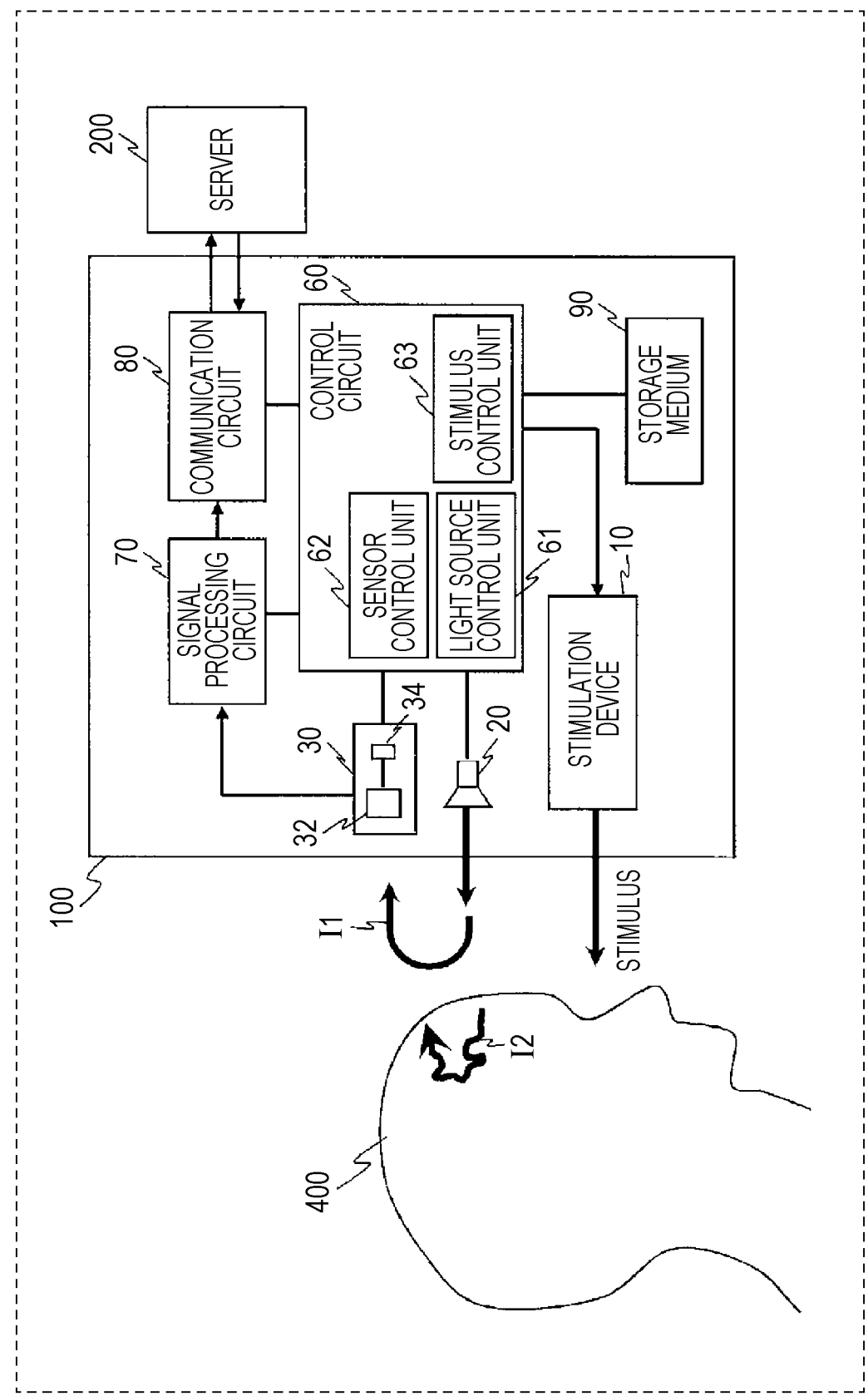
FIG. 1B is a schematic diagram illustrating a biometric system according to the exemplary embodiment of the present disclosure.

FIG. 1B is a schematic diagram illustrating a biometric system according to an exemplary embodiment of the present disclosure. The biometric system includes the biometric apparatus 100 and a server 200. The biometric apparatus 100 includes a stimulation device 10, the light source 20, the image sensor 30, the control circuit 60, the signal processing circuit 70, a communication circuit 80, and a storage medium 90. The server 200 is a computer provided at a place different from a place at which the biometric apparatus 100 is provided. The server 200 can be connected to the biometric apparatus 100 over a network such as a local area network (LAN) or the Internet.

The stimulation device 10 gives a visual stimulus or an audio stimulus, for example, to a user who is a target. The stimulation device 10 can be, for example, a display, a speaker, or another electronic device. The stimulation device 10 may be an element outside the biometric apparatus 100, instead. The light source 20 emits a light pulse radiated onto a target part including the user's head and face. The light source 20 is not limited to a single light emitting device, and may be achieved by a combination of light emitting devices. The image sensor 30 detects at least a part of the light pulse returning from the target part of the user and outputs image data. The image sensor 30 includes pixels. The pixels each include a photoelectric conversion element 32 and one or more charge accumulation units 34. The signal processing circuit 70 performs various processes based on image data output from the image sensor 30. The communication circuit 80 includes a network interface controller, for example, and communicates with an external apparatus such as the server 200. The storage medium 90 includes a memory such as a RAM or a ROM. The storage medium 90 stores programs that specify processes performed by the control circuit 60 and the signal processing circuit 70 and various types of data generated in the course of the processes. The control circuit 60 is connected to the stimulation device 10, the light source 20, the image sensor 30, the signal processing circuit 70, the communication circuit 80, and the storage medium 90. The control circuit 60 controls the operation of the entirety of the biometric apparatus 100.

The control circuit 60 according to the present embodiment includes a light source control unit 61 that controls the light source 20, a sensor control unit 62 that controls the image sensor 30, and a stimulation control unit 63 that controls the stimulation device 10. The light source control unit 61, the sensor control unit 62, and the stimulation control unit 63 may be achieved by three discrete circuits or a single circuit. The light source control unit 61, the sensor control unit 62, and the stimulation control unit 63 may each be achieved by executing a control program stored in the storage medium 90, such as a memory, using the control circuit 60.

The light source control unit 61 controls intensity, pulse width, emission timings, and/or wavelength of light pulses emitted from the light source 20. The sensor control unit 62 controls timings at which each pixel of the image sensor 30 accumulates signals. The stimulation control unit 63 controls a stimulus to be given to the stimulation device 10 and timings of the stimulus. The stimulation control unit 63 controls, for example, at least hue, saturation, or luminosity of aa video given as the stimulus or at least either quality or volume of a sound given as the stimulus.

The signal processing circuit 70 generates data indicating the state of the target on the basis of image data output from the image sensor 30. The signal processing circuit 70 can transmit the data to the server 200 through the communication circuit 80. The signal processing circuit 70 can also read data accumulated in the server 200 through the communication circuit 80. The control circuit 60 can determine the stimulus to be given by the stimulation device 10 on the basis of the data generated by the signal processing circuit 70.

The server 200 accumulates data generated by the signal processing circuit 70 and data regarding content to be presented to the user. The content to be presented can include, for example, at least text information, video information, or sound information.

"Biometric information" herein refers to measurable amounts in a living body that vary in accordance with a stimulus. The biometric information includes various amounts such as blood flow, blood pressure, heart rate, pulse rate, respiratory rate, body temperature, brain waves, oxygenated hemoglobin concentration in blood, deoxygenated hemoglobin concentration in blood, blood oxygen saturation, and skin reflectance spectrum. Some pieces of the biometric information are called "vital signs".

The components of the biometric apparatus 100 will be described more specifically hereinafter.

1-1. Stimulation Device 10

The stimulation device 10 gives a stimulus to the user. The stimulation device 10 may be configured to give a stimulus to more than one user. The stimulus given by the stimulation device 10 causes a biological reaction in the user. The stimulation device 10 may present information determined on the basis of the biological reaction in the user, such as content, to the user or a person other than the user. In the example illustrated in FIG. 1B, the biometric apparatus 100 includes the stimulation device 10, but a part or the entirety of the stimulation device 10 may be provided outside the biometric apparatus 100, instead.

The stimulation device 10 can be a head-mounted device, a goggle, a headset device, or a device including a display such as a smartphone. The stimulation device 10 may be an audio device, a lighting device, or an air conditioning device, instead. The stimulation device 10 may include devices that give different stimuli. The stimulation device 10 can give the user at least one of stimuli including, for example, a video, text, sound such as music or voice, brightness, heat, cold, humidity, dryness, vibration, and wind. A video and text are visual stimuli. Sound is an audio stimulus. The stimulation device 10 including a display may give image, video, or sound content to the user. A visual stimulus can be, for example, a web advertisement, a moving image, or a video game. One of various problems such as calculation problem, a word problem, a puzzle, and a quiz may be given as a visual stimulus, instead. A problem may be specially created in order to examine a state of the brain activity of the target. The stimulation device 10 may output a sound associated with a problem while presenting the problem. A visual stimulus may be a change in brightness or color of lighting in a room, instead of video content or sound content.

A tactile stimulus, an olfactory stimulus, or a gustatory stimulus may be given instead of a visual stimulus or an audio stimulus. The stimulation device 10 has a structure and a function that differ in accordance with a type of stimulus to be given to the user. When the stimulation device 10 gives a tactile stimulus to the user, for example, the stimulation device 10 can be a device that generates vibration or heat. When the stimulation device 10 gives an olfactory stimulus to the user, the stimulation device 10 can be a device that generates a smell.

1-2. Light Source 20

The light source 20 radiates light onto the target part including the user's head, that is, more specifically, for example, the user's forehead. The light that has been emitted from the light source 20 and that has reached the user divides into a surface reflection component I1, which is reflected from a surface of the user, and an internal scattering component I2, which is scattered inside the user. The internal scattering component I2 is a component reflected or scattered once or subjected to multiple scattering inside a living body. When light is emitted to the user's head, the internal scattering component I2 refers to a component that reaches a part 8 to 16 mm deep into the user's head, that is, for example, the brain, and that returns to the biometric apparatus 100 again. The surface reflection component I1 includes three components, namely a direct reflection component, a diffusion reflection component, and a scattering reflection component. The direct reflection component is a reflection component whose angle of incidence and angle of reflection are the same. The diffusion reflection component is a component diffused and reflected by an uneven surface. The scattering reflection component is a component scattered and reflected by internal tissues near the surface. When light is emitted to the user's head, the scattering reflection component is a component scattered and reflected under an outer layer of the skin. The surface reflection component I1 reflected from the surface of the user can include these three components. Traveling directions of the surface reflection component I1 and the internal scattering component I2 change due to reflection and scattering, respectively, and parts of the surface reflection component I1 and the internal scattering component I2 reach the image sensor 30.

In the present embodiment, the surface reflection component I1 and the internal scattering component I2 of reflected light returning from the user's head are detected. The surface reflection component I1 reflects the appearance of the user's face. Changes in the appearance of the user's face, therefore, can be estimated by analyzing temporal changes in the surface reflection component I1. The intensity of the internal scattering component I2, on the other hand, varies in accordance with the brain activity of the user. The state of the brain activity of the user, therefore, can be estimated by analyzing temporal changes in the internal scattering component I2.

First, a method for obtaining the internal scattering component I2 will be described. The light source 20 repeatedly emits a light pulse at certain time intervals or certain timings in accordance with an instruction from the control circuit 60. The light pulse emitted from the light source 20 can be, for example, a rectangular wave whose falling period is close to zero. A "falling period" herein refers to a period from a beginning of a decrease in the intensity of a light pulse to an end of the decrease. In general, light incident on the user propagates through the user in various routes and is emitted from the surface of the user with a lag. A trailing edge of the internal scattering component I2 of a light pulse, therefore, has an extent. When the target part of the user is the forehead, the extent of the trailing edge of the internal scattering component I2 is about 4 ns. In consideration of this, the falling period of the light pulse can be set to half the extent or shorter, namely 2 ns or shorter. The falling period may be half this value or shorter, namely 1 ns or shorter, instead. A rising period of the light pulse emitted from the light source 20 may have any length. A "rising period" refers to a period from a beginning of an increase in the intensity of a light pulse to an end of the increase. In the detection of the internal scattering component I2 in the present embodiment, only a falling part of a light pulse is used, and a rising part is not used. A rising part of a light pulse can be used to detect the surface reflection component I1. The light source 20 can be, for example, a laser such as a laser diode (LD). Light emitted from the laser has steep time-response characteristics where a falling part of a light pulse is substantially perpendicular to a time axis.

Light emitted from the light source 20 can have any wavelength within a range of, for example, 650 to 950 nm. This wavelength range is included in a wavelength range of red to near infrared. The wavelength range is called a "biological window", where light is relatively not easily absorbed by water in a living body and the skin. When a living body is a detection target, detection sensitivity can be increased by using light within the above wavelength range. When changes in cerebral blood flow of the user are detected as in the present embodiment, light used is considered to be mainly absorbed by oxygenated hemoglobin ($HbO_2$) and deoxygenated hemoglobin (Hb). Wavelength dependence of light absorption is different between oxygenated hemoglobin and deoxygenated hemoglobin. In general, when there is a change in blood flow, the concentration of oxygenated hemoglobin and deoxygenated hemoglobin changes. A degree of light absorption also changes in accordance with these changes. When there is a change in blood flow, therefore, the amount of light detected also changes over time.

The light source 20 may emit light of a single wavelength within the above wavelength range or light of two or more wavelengths. The light of two or more wavelengths may be emitted from different light sources.

In general, absorption characteristics and scattering characteristics of biological tissues vary depending on the wavelength. A more detailed component analysis can therefore be conducted on a measurement target by detecting wavelength dependence of light signals based on the internal scattering component I2. In biological tissues, for example, absorbance of oxygenated hemoglobin ($HbO_2$) is higher than that of deoxygenated hemoglobin (Hb) at a wavelength of 805 nm or longer. At a wavelength of 805 nm or shorter, on the other hand, opposite characteristics are observed. The light source 20 may therefore be configured, for example, to emit light of a wavelength around 750 nm and light of a wavelength around 850 nm. In this case, light intensity of the internal scattering component I2 based on the light of a wavelength around 750 nm and light intensity of the internal scattering component I2 based on a wavelength around 850 nm are measured. The signal processing circuit 70 can obtain an amount of change in the concentration of $HbO_2$ and Hb in blood from initial values by solving predetermined simultaneous equations on the basis of signal values of light intensity input from each pixel.

In the biometric apparatus 100 according to the present embodiment, cerebral blood flow of the user is measured in a noncontact manner. A light source 20 designed in consideration of an effect upon the retina, therefore, can be used. For example, a light source 20 that satisfies Class 1 of laser safety regulations made in various countries can be used. When Class 1 is satisfied, low light whose accessible emission limit (AEL) is below 1 mW is radiated onto the user. It is to be noted that the light source 20 itself need not satisfy Class 1. For example, Class 1 of the laser safety regulations may be satisfied by providing a diffusion plate or a natural-density (ND) filter in front of the light source 20 and diffusing or attenuating light.

Streak cameras have been conventionally used to separately detect information such as absorption coefficients or diffusion coefficients in a living body at different positions in a depth direction. For example, Japanese Unexamined Patent Application Publication No. 4-189349 discloses an example of such a streak camera. In these streak cameras, ultrashort light pulses whose pulse width is femtoseconds or picoseconds are used in order to perform measurement with a desired level of spatial resolution.

The biometric apparatus 100 according to the present embodiment, on the other hand, can separately detect the surface reflection component I1 and the internal scattering component I2. Light pulses emitted by the light source 20, therefore, need not be ultrashort light pulses, and any pulse width may be selected as desired.

When the user's head is irradiated with light in order to measure cerebral blood flow, the amount of light of the internal scattering component I2 can be an extremely small value such as one-thousandth or one-ten-thousandth of that of the surface reflection component I1. Furthermore, the amount of light that can be radiated needs to be extremely small in consideration of laser safety regulations. The detection of the internal scattering component I2 is therefore extremely difficult. Even this case, the accumulated amount of the internal scattering component I2 accompanying a lag can be increased by emitting, from the light source 20, light pulses whose pulse width is relatively large. The amount of light detected can thus be increased, thereby increasing a sound-to-noise (S/N) ratio.

Figure 2:
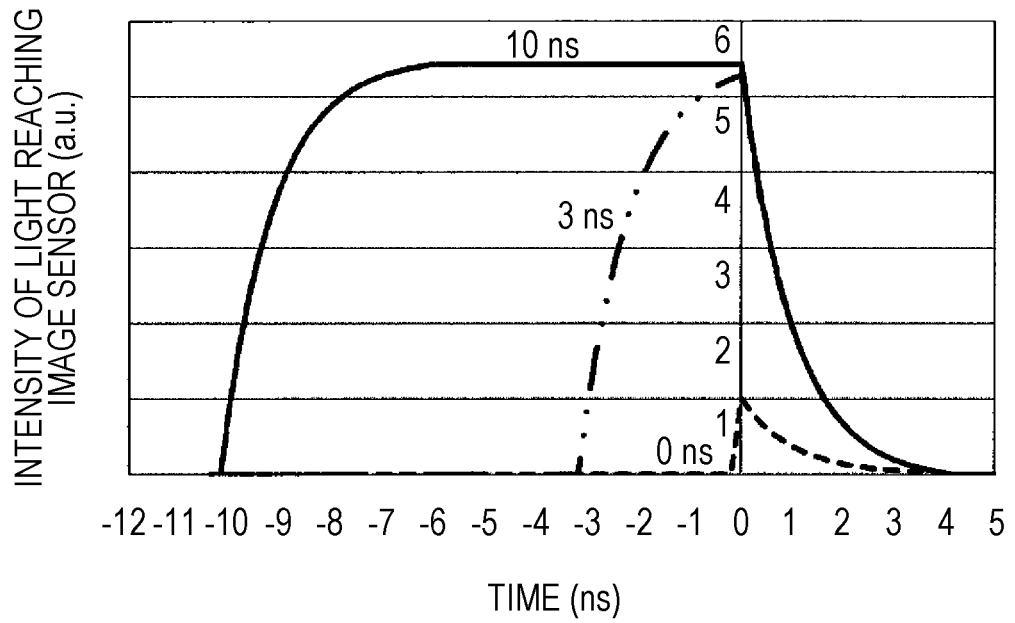
FIG. 2 is a diagram illustrating an example of temporal changes in the intensity of light that reaches an image sensor.

The light source 20 emits, for example, light pulses whose pulse width is 3 ns or greater. In general, a temporal extent of light scattered inside biological tissues such as the brain is about 4 ns. FIG. 2 is a diagram illustrating an example of temporal changes in the intensity of light that reaches the image sensor 30. FIG. 2 illustrates an example in which the width of an input light pulse emitted from the light source 20 is 0 ns, 3 ns, and 10 ns. As illustrated in FIG. 2, the amount of light of the surface reflection component I2 that appears in a trailing edge of a light pulse returning from the user increases as the width of the light pulses from the light source 20 increases.

Figure 3:
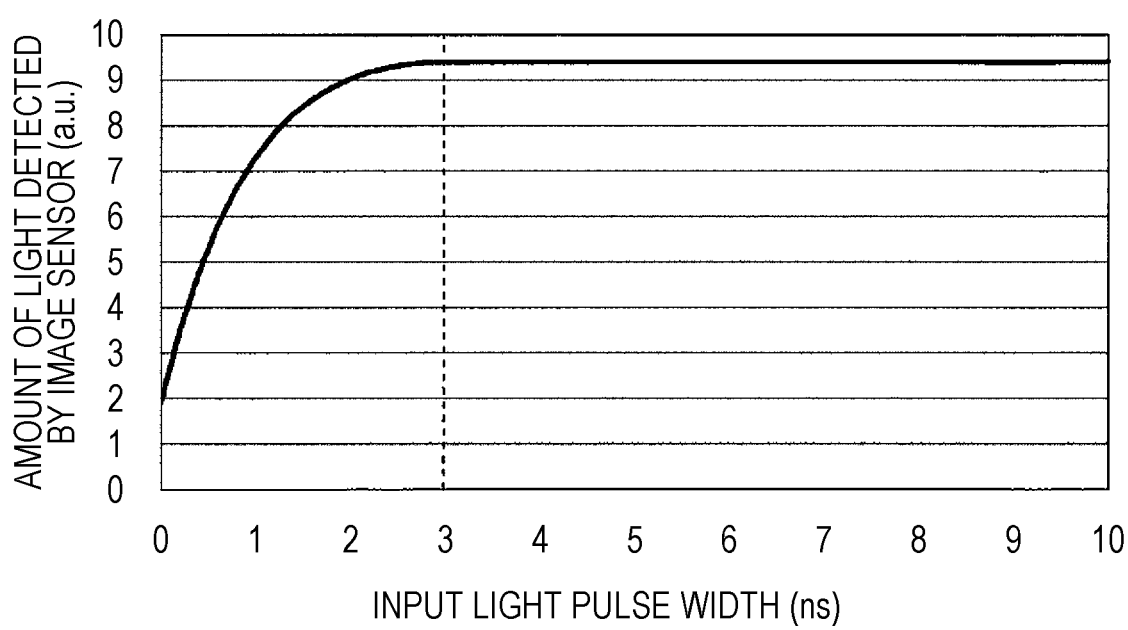
FIG. 3 is a graph illustrating dependence of the amount of light detected by the image sensor on the width of an input light pulse.

FIG. 3 is a diagram in which a horizontal axis represents the width of an input light pulse and a vertical axis represents the amount of light detected by the image sensor 30. The image sensor 30 includes an electronic shutter. Results illustrated in FIG. 3 were obtained when the electronic shutter were opened 1 ns after a trailing edge of a light pulse was reflected from the surface of the user and reached the image sensor 30. A reason why this condition was selected is that the percentage of the surface reflection component I1 is higher than that of the internal scattering component I2 immediately after the trailing edge of the light pulse reaches the image sensor 30. As illustrated in FIG. 3, the amount of light detected can be maximized when the pulse width of the light pulse emitted from the light source 20 is 3 ns or greater.

The light source 20 may emit a light pulse whose pulse width is 5 ns or greater, or 10 ns or greater. When the pulse width is too great, on the other hand, the amount of light wasted increases. The light source 20, therefore, emits a light pulse whose pulse width is, for example, 50 ns or smaller. Alternatively, the light source 20 may emit a light pulse whose pulse width is 30 ns or smaller, or 20 ns or smaller.

A radiation pattern employed by the light source 20 may be, for example, a pattern having a uniform intensity distribution in an irradiation area. In this respect, the biometric apparatus 100 according to the present embodiment is different from a conventional biometric apparatus such as one disclosed in Japanese Unexamined Patent Application Publication No. 11-164826. In the apparatus disclosed in Japanese Unexamined Patent Application Publication No. 11-164826, an image sensor and a light source are 3 cm away from each other and a surface reflection component is spatially separated from an internal scattering component. As a result, radiation inevitably becomes discrete. The biometric apparatus 100 according to the present embodiment, on the other hand, can temporally separate the surface reflection component I1 from the internal scattering component I2 and reduce the surface reflection component I1. A light source 20 that employs a radiation pattern having a uniform intensity distribution, therefore, can be used. The radiation pattern having a uniform intensity distribution may be formed by diffusing light emitted from the light source 20 with a diffusion plate.

In the present embodiment, unlike in the example of the related art, the internal scattering component I2 can be detected directly below an irradiation point on the user. Measurement resolution can also be increased by spatially irradiating the user with light over a wide range.

1-3. Image Sensor 30

The image sensor 30 detects at least a part of a reflected light pulse returning from the user's head with each pixel. The image sensor 30 outputs signals according to the intensity of detected light for each pixel. The signals include a signal according to an intensity included in at least a part of a rising period of the reflected light pulse and a signal according to an intensity included in at least a part of a falling period.

The image sensor 30 includes light detection cells arranged in two dimensions and can obtain two-dimensional information regarding the user at once. The light detection cells each include a photoelectric conversion element and one or more charge accumulation units. The light detection cells will also be referred to as "pixels" herein. The image sensor 30 can be, for example, any imaging device such as a charge-coupled device (CCD) image sensor or a complementary metal-oxide-semiconductor (CMOS) image sensor.

The image sensor 30 includes an electronic shutter. The electronic shutter is a circuit that controls imaging timings. In the present embodiment, the sensor control unit 62 of the control circuit 60 has a function of an electronic shutter. The electronic shutter controls a signal accumulation period, in which received light is converted into effective electrical signals and accumulated, and a period in which the accumulation of signals is stopped. The signal accumulation period can also be referred to as an "exposure period". In the following description, the width of an exposure period might be referred to as "shutter width". A period from an end of an exposure period to a beginning of a next exposure period might be referred to as a "non-exposure period". An exposed state might be referred to as "open", and a state in which exposure is stopped might be referred to as "close" hereinafter.

The image sensor 30 can adjust exposure periods and non-exposure periods in sub-nanoseconds, namely 30 ps to 1 ns, for example, using the electronic shutter. A conventional time-of-flight (ToF) camera intended for measurement of distance detects the entirety of light emitted from the light source 20 and reflected and returning from a subject in order to measure distance regardless of the brightness of the subject. In a conventional ToF camera, therefore, shutter width needs to be greater than the pulse width of light. With the biometric apparatus 100 according to the present embodiment, on the other hand, the amount of light from a subject need not be corrected. Shutter width, therefore, need not be greater than pulse width. Shutter width may be set to a value, for example, larger than or equal to 1 ns and smaller than or equal to 30 ns. Since shutter width can be reduced with the biometric apparatus 100 according to the present embodiment, an effect of dark current included in detected signals can be reduced.

When the user's forehead is irradiated with light and information such as cerebral blood flow is detected, an attenuation rate of light inside a living body is considerably high. For example, outgoing light can be attenuated to about one-millionth of incident light. In order to detect the internal scattering component I2, therefore, the amount of light might be insufficient with radiation of one pulse alone. The amount of light is especially small in radiation according to Class 1 of the laser safety regulations. In this case, detected signals can be accumulated and sensitivity can be improved by repeatedly emitting a light pulse using the light source 20 and accordingly repeatedly exposing the image sensor 30 using the image sensor 30.

An example of the configuration of the image sensor 30 will be described hereinafter.

The image sensor 30 can include pixels arranged on an imaging surface in two dimensions. The pixels can each include, for example, a photoelectric conversion element such as a photodiode and one or more charge accumulation units. An example will be described hereinafter in which each pixel includes a photoelectric conversion element that generates, through photoelectric conversion, signal charge according to the amount of light received, a charge accumulation unit that accumulates signal charge generated from the surface reflection component I1 of light pulses, and a charge accumulation unit that accumulates signal charge generated from the internal scattering component I2 of the light pulses. In the following example, the control circuit 60 causes the image sensor 30 to detect the surface reflection component I1 by causing the image sensor 30 to detect a part of a light pulse before a falling period, the light pulse being returning from the user's head. The control circuit 60 also causes the image sensor 30 to detect the internal scattering component I2 by causing the image sensor 30 to detect a part of the light pulse after the falling period, the light pulse being returning from the user's head. The light source 20 in this example emits light of two wavelengths.

Figure 4A:
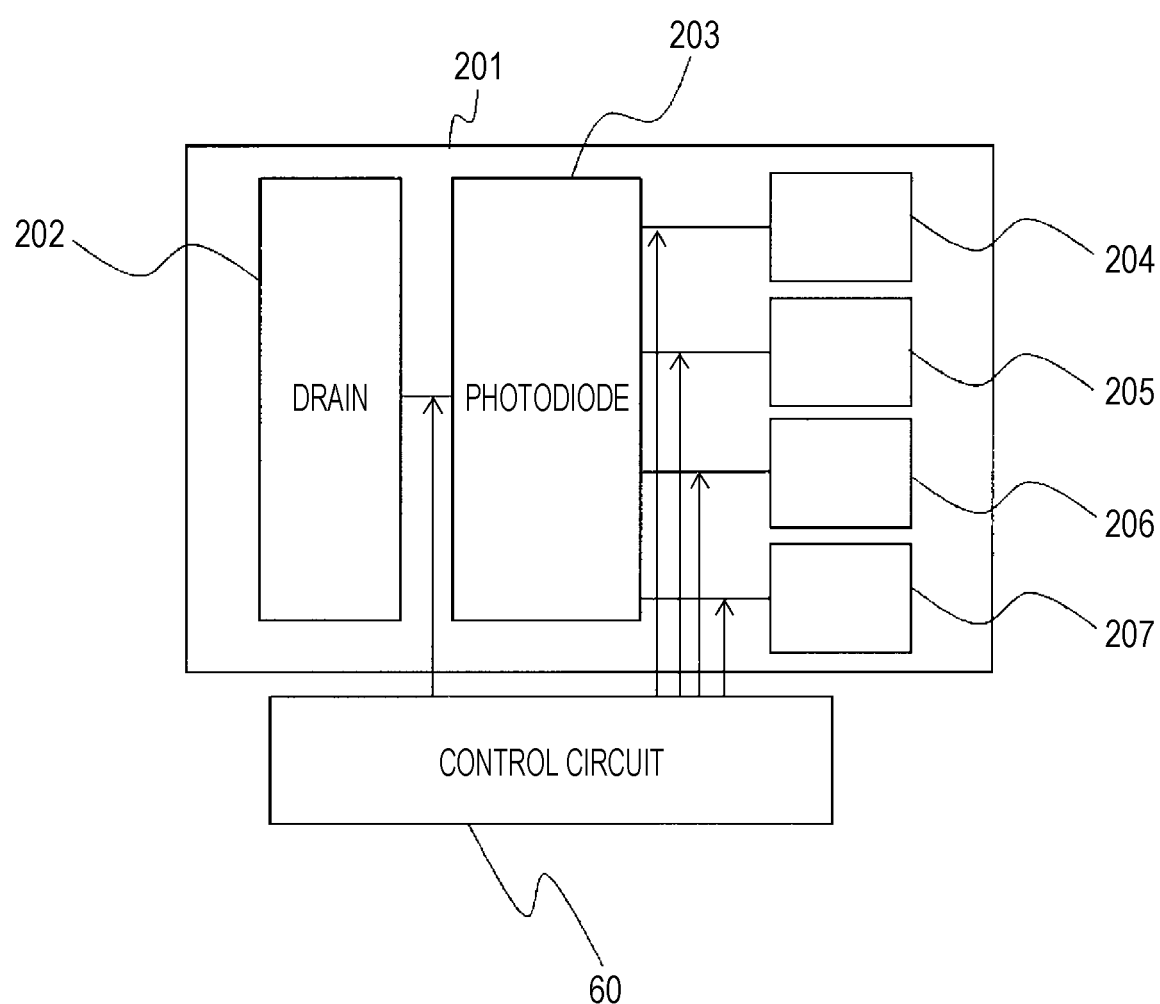
FIG. 4A is a diagram illustrating an example of a schematic configuration of each of pixels of the image sensor.

FIG. 4A is a diagram illustrating an example of a schematic configuration of a pixel 201 included in the image sensor 30. FIG. 4A schematically illustrates the configuration of the pixel 201 and does not necessarily reflect actual configuration. The pixel 201 in this example includes a photodiode 203 that performs photoelectric conversion, a first floating diffusion layer 204, a second floating diffusion layer 205, a third floating diffusion layer 206, and a fourth floating diffusion layer 207, which are charge accumulation units, and a drain 202 to which signal charge is discharged.

Photons incident on each pixel as a result of emission of a light pulse are converted by the photodiode 203 into signal electrons, which are signal charge. The obtained signal electrons are discharged to the drain 202 or distributed to the first floating diffusion layer 204, the second floating diffusion layer 205, the third floating diffusion layer 206, or the fourth floating diffusion layer 207 in accordance with a control signal input from the control circuit 60.

The emission of a light pulse from the light source 20, the accumulation of signal charge in the first floating diffusion layer 204, the second floating diffusion layer 205, the third floating diffusion layer 206, and the fourth floating diffusion layer 207, and the discharge of signal charge to the drain 202 are repeated in this order. The repetition is performed at high speed, namely, for example, tens of thousands to hundreds of millions of times in one frame (e.g., about ⅓₀ second) of a moving image. The pixel 201 ultimately generates four image signals based on signal charge accumulated in the first floating diffusion layer 204, the second floating diffusion layer 205, the third floating diffusion layer 206, and the fourth floating diffusion layer 207 and outputs the image signals.

The control circuit 60 in this example causes the light source 20 to sequentially emit a first light pulse of a first wavelength and a second light pulse of a second wavelength repeatedly. The state of the user can be analyzed by selecting, as the first and second wavelengths, two wavelengths at which the absorbance of internal tissues of the user is different. For example, a wavelength longer than 805 nm may be selected as the first wavelength, and a wavelength shorter than 805 nm may be selected as the second wavelength. As a result, changes in the concentration of oxygenated hemoglobin and the concentration of deoxygenated hemoglobin in the user's blood can be detected.

Figure 5:
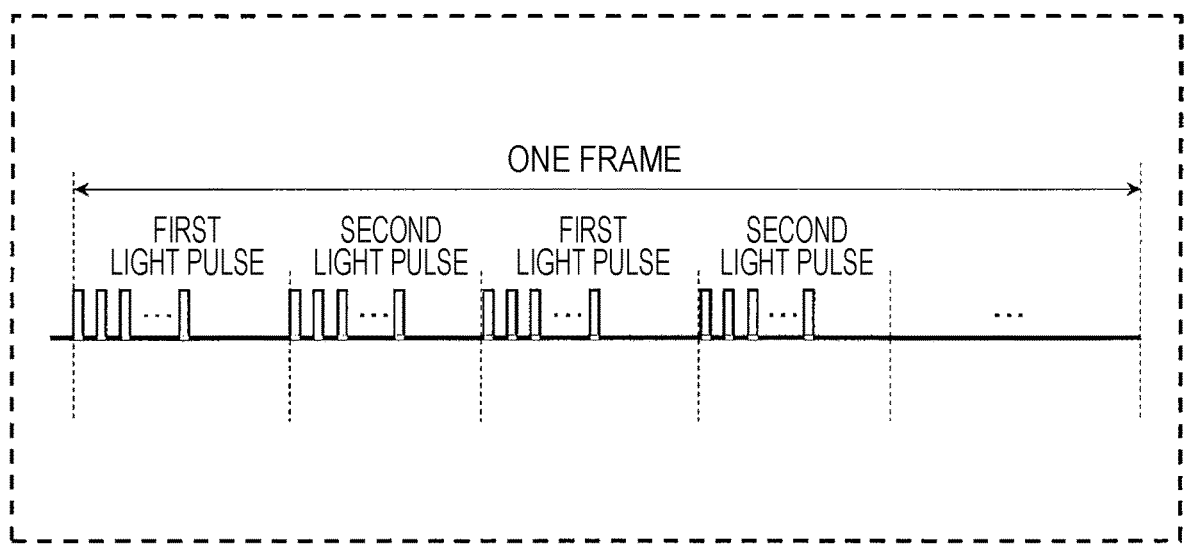
FIG. 5 is a diagram illustrating an example of an operation performed in each frame.

As illustrated in FIG. 5, first, the control circuit 60 causes the light source 20 to emit the first light pulse. The control circuit 60 causes the first floating diffusion layer 204 to accumulate signal charge in a first period in which a surface reflection component I1 of the first light pulse is incident on the photodiode 203. Next, the control circuit 60 causes the second floating diffusion layer 205 to accumulate signal charge in a second period in which an internal scattering component I2 of the first light pulse is incident on the photodiode 203. Next, the control circuit 60 causes the light source 20 to emit the second light pulse. The control circuit 60 causes the third floating diffusion layer 206 to accumulate signal charge in a third period in which a surface reflection component I1 of the second light pulse is incident on the photodiode 203. Next, the control circuit 60 causes the fourth floating diffusion layer 207 to accumulate signal charge in a fourth period in which an internal scattering component I2 of the second light pulse is incident on the photodiode 203.

The control circuit 60 thus causes the first floating diffusion layer 204 and the second floating diffusion layer 205 to sequentially accumulate signal charge from the photodiode 203 after starting the emission of the first light pulse. The control circuit 60 then causes the third floating diffusion layer 206 and the fourth floating diffusion layer 207 to sequentially accumulate signal charge from the photodiode 203 a certain period of time after starting the emission of the second light pulse. The above operation is repeated. In order to estimate the amount of disturbance light and ambient light, a period may be provided in which signal charge is accumulated in another floating diffusion layer that is not illustrated with the light source 20 turned off. By subtracting the amount of signal charge in the other floating diffusion layer from the amount of signal charge in the first floating diffusion layer 204, the second floating diffusion layer 205, the third floating diffusion layer 206, and the fourth floating diffusion layer 207, a signal from which disturbance light and ambient light components have been removed can be obtained.

Although there are four charge accumulation units in the present embodiment, any plural number of charge accumulation units may be provided in accordance with desired purposes. When only one wavelength is used, for example, the number of charge accumulation units may be two. When only one wavelength is used and the surface reflection component I1 need not be detected, the number of charge accumulation units in each pixel may be one. Even when two or more wavelengths are used, the number of charge accumulation units may be one if imaging employing the wavelengths is performed in different frames. When the detection of the surface reflection component I1 and the detection of the internal scattering component I2 are performed in different frames, the number of charge accumulation units may be one.

Figure 4B:
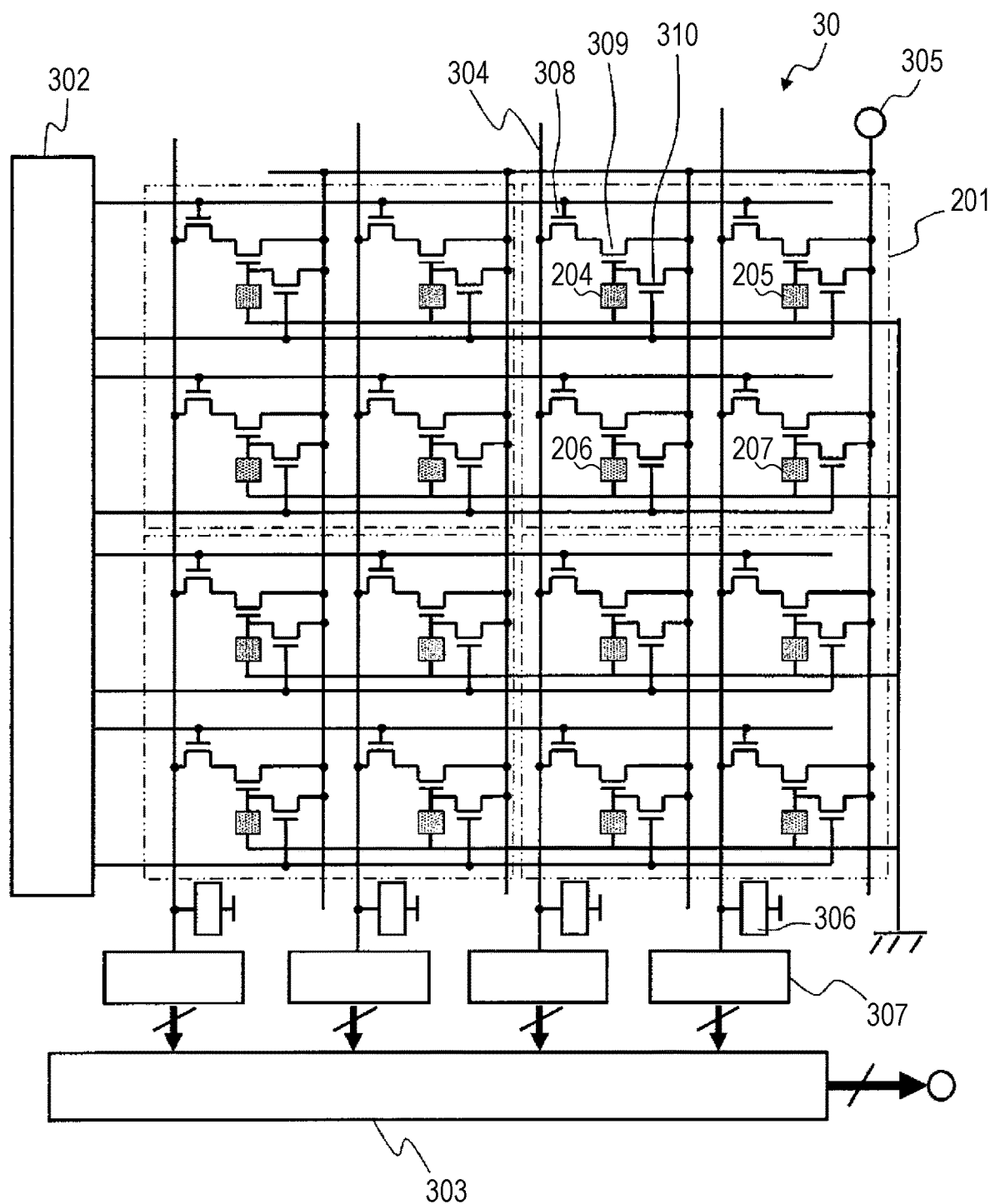
FIG. 4B is a diagram illustrating an example of the configuration of the image sensor.

FIG. 4B is a diagram illustrating an example of the configuration of the image sensor 30. In FIG. 4B, areas defined by dash-dot-dot lines correspond to the pixels 201. The pixels 201 each include a photodiode. Although FIG. 4B illustrates only four pixels arranged in two rows and two columns, more pixels can be provided in practice. The pixels 201 each include the first floating diffusion layer 204, the second floating diffusion layer 205, the third floating diffusion layer 206, and the fourth floating diffusion layer 207. Signals accumulated in the first floating diffusion layer 204, the second floating diffusion layer 205, the third floating diffusion layer 206, and the fourth floating diffusion layer 207 are treated like signals of four pixels of a common CMOS image sensor and output from the image sensor 30.

The pixels 201 each include four signal detection circuits. The signal detection circuits each include a source follower transistor 309, a row selection transistor 308, and a reset transistor 310. In this example, the reset transistor 310 corresponds to the drain 202 illustrated in FIG. 4A, and a pulse input to a gate of the reset transistor 310 corresponds to a pulse discharged to the drain 202. Each transistor is a field-effect transistor formed on a semiconductor board, for example, but is not limited to this. As illustrated in FIG. 4B, either an input terminal or an output terminal (typically a source) of the source follower transistor 309 and either an input terminal or an output terminal (typically a drain) of the row selection transistor 308 are connected to each other. A gate of the source follower transistor 309, which is a control terminal, is connected to the photodiode 203. Signal charge (i.e., holes or electrons) generated by the photodiode 203 is accumulated in a floating diffusion layer, which is a charge accumulation unit, between the photodiode 203 and the source follower transistor 309.

The first floating diffusion layer 204, the second floating diffusion layer 205, the third floating diffusion layer 206, and the fourth floating diffusion layer 207 are connected to the photodiode 203. Switches can be provided between the photodiode 203 and the first floating diffusion layer 204, the second floating diffusion layer 205, the third floating diffusion layer 206, and the fourth floating diffusion layer 207. The switches are used to switch, in accordance with signal accumulation pulses from the control circuit 60, conduction states between the photodiode 203 and the first floating diffusion layer 204, the second floating diffusion layer 205, the third floating diffusion layer 206, and the fourth floating diffusion layer 207. Starting and stopping of accumulation of signal charge in the first floating diffusion layer 204, the second floating diffusion layer 205, the third floating diffusion layer 206, and the fourth floating diffusion layer 207 are thus controlled. The electronic shutter in the present embodiment has a mechanism for this exposure control.

Signal charge accumulated in the first floating diffusion layer 204, the second floating diffusion layer 205, the third floating diffusion layer 206, and the fourth floating diffusion layer 207 is read when a row selection circuit 302 turns on gates of the row selection transistors 308. At this time, currents flowing from a source follower power supply 305 into the source follower transistors 309 and source follower loads 306 are amplified in accordance with signal potential of the first floating diffusion layer 204, the second floating diffusion layer 205, the third floating diffusion layer 206, and the fourth floating diffusion layer 207. Analog signals based on these currents read from vertical signal lines 304 are converted by analog-to-digital (A/D) conversion circuit 307, each of which is connected in each column, into digital signal data. A column selection circuit 303 reads the digital signal data for each column, and the image sensor 30 outputs the digital signal data. The row selection circuit 302 and the column selection circuit 303 sequentially read information regarding signal charge accumulated in the floating diffusion layers row by row. After all signal charge is read, the control circuit 60 turns on the gates of the reset transistors 310 to reset all the floating diffusion layers. As a result, imaging in one frame is completed. The image sensor 30 then repeats high-speed imaging for subsequent frames to complete the imaging in the frames.

Although a CMOS image sensor 30 is taken as an example in the present embodiment, the image sensor 30 may be an imaging device of a different type, instead. The image sensor 30 may be, for example, a CCD image sensor, a single-photon counting device, or an amplified image sensor (e.g., an electron multiplying CCD (EMCCD) or an intensified CCD (ICCD)), instead.

FIG. 5 is a diagram illustrating an example of an operation performed in each frame in the present embodiment. As illustrated in FIG. 5, the emission of the first light pulse and the emission of the second light pulse may alternate in each frame. In doing so, a difference between timings at which detected images are obtained at two wavelengths can be reduced, and imaging based on the first and second light pulses can be simultaneously performed even for a moving user.

In the present embodiment, the image sensor 30 detects both the surface reflection component I1 and the internal scattering component I2 of light pulses. First biological information regarding the user can be obtained from temporal or spatial changes in the surface reflection component I1. The first biological information indicates the appearance of the user's face and can be information regarding, for example, a line of sight, pupil diameter, blinking, or facial expression. Brain activity information, which is second biological information, regarding the user, on the other hand, can be obtained from temporal or spatial changes in the internal scattering component I2.

A signal indicating the first biological information might be referred to as a "first biological signal" herein. A signal indicating brain activity information might be referred to as a "brain activity signal" herein.

1-4. Control Circuit 60 and Signal Processing Circuit 70

The control circuit 60 adjusts a time difference between an emission timing of a light pulse from the light source 20 and a shutter timing of the image sensor 30. The time difference might be herein referred to as a "phase difference". The emission timing of the light source 20 refers to a timing at which a light pulse emitted from the light source 20 begins to rise. The shutter timing refers to a timing at which exposure starts. The control circuit 60 may adjust the phase difference by changing the emission timing or the shutter timing.

The control circuit 60 may be configured to remove an offset component from a signal detected by each pixel of the image sensor 30. The offset component is a signal component deriving from ambient light such as sunlight or light from a fluorescent light or disturbance light. The offset component caused by ambient light or disturbance light can be estimated by detecting a signal using the image sensor 30 with the light source 20 turned off, that is, without the light source 20 emitting light.

The control circuit 60 can be a combination of a processor and a memory, for example, or an integrated circuit including a processor and a memory, such as a microcontroller. The control circuit 60 adjusts emission timings and shutter timings, for example, by executing a program stored in the memory using the processor.

The signal processing circuit 70 processes image signals output from the image sensor 30. The signal processing circuit 70 performs arithmetic processing such as image processing. The signal processing circuit 70 can be achieved, for example, by a combination of a digital signal processor (DSP), a programmable logic device (PLD) such as a field-programmable gate array (FPGA), a central processing unit (CPU), or a graphics processing unit (GPU) and a computer program. The control circuit 60 and the signal processing circuit 70 may be a single integrated circuit or discrete circuits. The signal processing circuit 70 may be a component of an external apparatus provided at a remove place, such as a server. In this case, the external apparatus such as a server communicates data with the light source 20, the image sensor 30, and the control circuit 60 through wireless or wired communication.

The signal processing circuit 70 according to the present embodiment can generate moving image data indicating temporal changes in cerebral blood flow and moving image data indicating temporal changes in the appearance of the face on the basis of image data output from the image sensor 30 frame by frame. The signal processing circuit 70, however, may generate another type of information instead of the moving image data. For example, the signal processing circuit 70 may synchronize with another device and generate biological information such as cerebral blood flow, blood pressure, blood oxygen saturation, or heart rate. The signal processing circuit 70 may also estimate an offset component deriving from disturbance light and remove the offset component.

Changes in cerebral blood flow or a blood component such as hemoglobin and human neural activity are known to have a close relationship. When a person's neural activity changes in accordance with a degree of interest of the person, for example, cerebral blood flow or a blood component changes. If biological information such as cerebral blood flow or appearance information regarding the face can be measured, therefore, a psychological state or a physical state of a user can be estimated. The psychological state can be, for example, moods, emotions, a health state, or temperature sensation. The moods can include, for example, comfort and discomfort. The emotions can include, for example, relief, anxiety, sadness, and anger. The health state can include, for example, healthy and weary. The temperature sensation can include, for example, hot, cold, and humid. The psychological states can also include indices of degrees of brain activity, such as interest, expertise, proficiency, and concentration. Furthermore, the signal processing circuit 70 can also estimate a physical state such as a degree of fatigue, sleepiness, or intoxication. The signal processing circuit 70 can estimate the psychological state or the physical state of the user on the basis of changes in cerebral blood flow or the appearance of the face and output a signal indicating a result of the estimation.

Figure 6A:
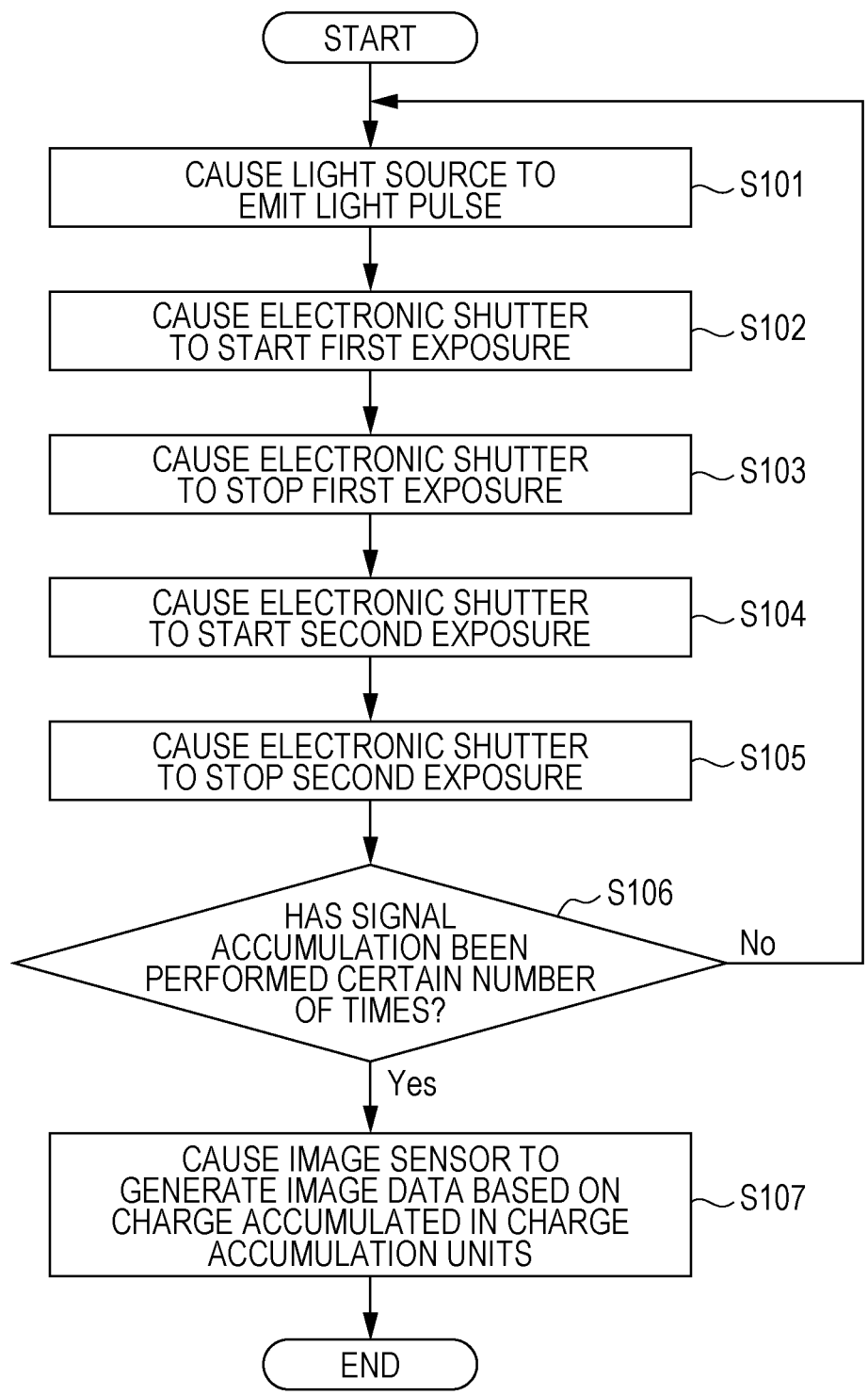
FIG. 6A is a flowchart illustrating an outline of control performed on a light source and the image sensor.

FIG. 6A is a flowchart illustrating an outline of control performed by the control circuit 60 on the light source 20 and the image sensor 30. An operation performed when the surface reflection component I1 and the internal scattering component I2 of reflected light are detected by each pixel using light of a single wavelength will be described hereinafter for the sake of simplicity. In this example, each pixel of the image sensor 30 includes a first charge accumulation unit that accumulates charge generated from the surface reflection component I1 and a second charge accumulation unit that accumulates charge generated from the internal scattering component I2.

In step S101, first, the control circuit 60 causes the light source 20 to emit a light pulse for a certain period of time. At this time, the electronic shutter of the image sensor 30 has stopped exposure. The control circuit 60 causes the electronic shutter to stop exposure until the light pulse is reflected from the surface of the user and begins to reach the image sensor 30.

Next, in step S102, the control circuit 60 causes the electronic shutter to start exposure at a certain timing before a falling period starts after the reflected light pulse begins to reach the image sensor 30. This exposure will be referred to as "first exposure". A timing at which the first exposure starts can be appropriately set for each pixel by measuring a distance to a target part for the pixel in advance. The timing at which the first exposure starts may be different between the pixels in accordance with a degree of curvature of a surface of the target part or the same between the pixels. Light detected as a result of the first exposure is mainly light that is scattered on a surface of the skin of the target part and that reaches the image sensor 30.

After a certain period of time elapses, in step S103, the control circuit 60 causes the electronic shutter to stop the first exposure. A timing at which the electronic shutter stops the first exposure can be, for example, before a falling period of the reflected light pulse starts.

Next, in step S104, the control circuit 60 causes the electronic shutter to start second exposure at a timing at which a part of the light pulse is scattered inside the user and reaches the image sensor 30. More specifically, the control circuit 60 causes the electronic shutter to start the second exposure after the falling period of the reflected light pulse starts. The timing at which the electronic shutter starts the second exposure can be calculated on the basis of the distance to the target part measured for each pixel in advance. The timing at which the electronic shutter starts the second exposure, too, may be different between the pixels in accordance with the degree of curvature of the surface of the target part or may be the same.

After a certain period of time elapses, in step S105, the control circuit 60 causes the electronic shutter to stop the second exposure. The length of the first exposure and the length of the second exposure may be the same or different from each other. In general, the amount of light of the surface reflection component I1 detected in the first exposure is larger than the amount of light of the internal scattering component I2 detected in the second exposure. The length of the first exposure, therefore, may be set shorter than the length of the second exposure.

Next, in step S106, the control circuit 60 determines whether the number of times that the above signal accumulation process has been performed has reached a certain value. If a result of the determination is No, the control circuit 60 repeats steps S101 to S105 until the result of the determination becomes Yes. An appropriate number of times is set in accordance with detection sensitivity of the internal scattering component I2. If the result of step S106 is Yes, the control circuit 60 causes, in step S107, the image sensor 30 to generate an image signal based on signal charge accumulated in the charge accumulation units. The image sensor 30 outputs first image data based on charge accumulated in the first charge accumulation unit of each pixel and second image data based on charge accumulated in the second charge accumulation unit of each pixel.

As a result of the above operation, a component of light scattered near the surface of the target part and a component light scattered inside the target part can be sensitively detected. The emission and exposure need not necessarily be repeatedly performed, and may be performed as necessary.

The signal processing circuit 70 generates first moving image data indicating changes in the appearance of the user's face by performing necessary image processing on the first image data, such as color correction, pixel interpolation, or frame interpolation. The signal processing circuit 70 also generates second moving image data indicating changes in a state of cerebral blood flow of the user by performing necessary image processing on the second image data. The signal processing circuit 70 then estimates the psychological state or the physical state of the user on the basis of the first moving image data and the second moving image data. For example, the user's state such as interest or concentration can be estimated on the basis of changes in facial expression or a line of sight estimated from the first moving image data and changes in brain activity estimated from the second moving image data. Details of these processes will be described later.

The signal processing circuit 70 may perform a process for changing the resolution of at least either the first image data or the second image data. For example, the signal processing circuit 70 may perform a process for making the resolution of the first image data higher than that of the second image data. The process for changing the resolution may be performed on only a part of each image. That is, the signal processing circuit 70 may perform a process for changing the resolution of at least a part of an image indicated by the first image data and/or the resolution of at least a part of an image indicated by the second image data. In this case, the signal processing circuit 70 generates data indicating a state of the target on the basis of temporal changes in the first image data and the second image data after the process. An example of such a process will be described hereinafter.

FIG. 6B is a flowchart illustrating an example of the process for changing the resolution of the first image data and the second image data. The signal processing circuit 70 in this example changes the resolution of the first and second image data by performing steps S108 to S114 illustrated in FIG. 6B. As a result of this process, the signal processing circuit 70 can make the resolution of the first image data higher than that of the second image data. The steps will be described hereinafter.

In step S108, the signal processing circuit 70 obtains first image data and second image data generated by the image sensor 30.

In step S109, the signal processing circuit 70 selects a necessary area of the first image data. When line-of-sight data is to be obtained, for example, an area around an eyeball is selected.

In step S110, the signal processing circuit 70 performs high-resolution processing on the first image data in the selected area. By performing a known super-resolution processing, for example, the signal processing circuit 70 makes the resolution of the first image data higher than that of the second image data. Alternatively, the signal processing circuit 70 may decrease the resolution of the first image data. In this case, by suppressing a decrease rate of the resolution of the first image data, the signal processing circuit 70 may make the resolution of the first image data higher than that of the second image data.

In step S111, the signal processing circuit 70 selects a necessary area of the second image data. For example, the signal processing circuit 70 selects an area corresponding to a part of the target's forehead.

In step S112, the signal processing circuit 70 performs low-resolution processing on the second image data. In order to reduce resolution, an arithmetic mean of signal values of neighboring pixels can be obtained. By obtaining an arithmetic mean, noise included in weak cerebral blood flow signals can be reduced.

In step S113, the signal processing circuit 70 outputs the processed first and second image data. For example, the signal processing circuit 70 stores the processed first image data and second image data in the storage medium 90.

In step S114, the signal processing circuit 70 determines whether the process has ended. If a result of the determination is No, the signal processing circuit 70 repeats steps S108 to S113 until the result of the determination becomes Yes. Whether the process has ended can be determined on the basis of, for example, whether the image sensor 30 has output image data or whether the user has given a stop instruction. Alternatively, whether the process has ended may be determined on the basis of whether a predetermined period of time has elapsed since a beginning of measurement or whether the amount of data accumulated since the beginning of the measurement has reached a predetermined value.

The signal processing circuit 70 may change the resolution of only either the first image data or the second image data. When the resolution of the first image data is increased and the resolution of the second image data is reduced, the amount of data can be reduced, and high-resolution appearance information regarding the face can be obtained.

A first frame rate at which the image sensor 30 outputs the first image data and a second frame rate at which the image sensor 30 outputs the second image data may be different from each other.

FIG. 6C is a flowchart illustrating an outline of a process for outputting image data while changing a frame rate using the image sensor 30 and then generating moving image data using the signal processing circuit 70.

In step S115, the image sensor 30 outputs first image data based on the surface reflection component I1 at a high frame rate. In this case, in order to increase the frame rate, the control circuit 60 shortens total exposure time in each frame by adjusting the shutter timings of the image sensor 30. Alternatively, in order to increase the frame rate, the control circuit 60 may increase each emission period and decrease the number of times of emission in each frame by adjusting the emission timings of the light source 20. The number of times of emission in each frame may be set to one by continuously emitting light in the frame.

When appearance information regarding the face is obtained, the light source 20 may be a light-emitting diode (LED). Laser light emitted from an LD or the like whose falling parts of light pulses are substantially perpendicular to a time axis need not necessarily be used to obtain appearance information regarding the face, and steep time-response characteristics are not mandatory.

In step S116, the signal processing circuit 70 generates appearance data regarding the face on the basis of the first image data output in step S115 and outputs the appearance data.

In step S117, the image sensor 30 outputs second image data based on the internal scattering component I2 at a low frame rate. In this case, in order to reduce the frame rate, the control circuit 60 makes total exposure time in each frame than when the first image data was obtained by adjusting the shutter timings of the image sensor 30.

In step S118, the signal processing circuit 70 generates cerebral blood flow data on the basis of the second image data obtained in step S117.

Alternatively, the image sensor 30 may output all frames at a high frame rate and then the signal processing circuit 70 may combine together image data from different frames and output the combined image data as a single set of image data, instead of outputting the second image data at a low frame rate.

The image sensor 30 and the signal processing circuit 70 repeat steps S115 to S118 until an instruction to end the measurement is received in step S119. The number of repetitions may be different between the first image and the second image.

1-5. Control Performed by Server 200 and Stimulation Device 10

The biometric apparatus 100 according to the present embodiment can be used in combination with the external server 200. The server 200 includes a storage device that accumulates data regarding content such as videos or sounds, video games, tests, or problems. The server 200 also includes a communication circuit that communicates with the communication circuit 80 of the biometric apparatus 100. The server 200 accumulates, in addition to data regarding moving images or applications to be provided for the user, moving image data and diagnosis data regarding brain activity generated by the signal processing circuit 70. Some or all of the functions of the server 200 may be incorporated into the biometric apparatus 100. Conversely, the server 200 may achieve some functions of the signal processing circuit 70 of the biometric apparatus 100.

The control circuit 60 includes a stimulus control unit 63. The stimulus control unit 63 can provide a stimulus such as a video or a sound to the user by controlling the stimulation device 10. The stimulus control unit 63 can control, for example, hue, saturation, or luminosity of video content to be given as a stimulus or a type, quality, or volume of sound content to be given as a stimulus.

The control circuit 60 can determine a stimulus to be given to the user next on the basis of the psychological state or the physical state of the user estimated by the signal processing circuit 70. If determining that a user who is watching a certain piece of content has lost interest or concentration, for example, the control circuit 60 can determine that another piece of content is to be displayed. This process may be performed by a processor included in the server 200. The control circuit 60 can obtain necessary data regarding a video or a sound from the server 200 and cause the stimulation device 10 to give a stimulus based on the data.

1-6. Modifications

The biometric apparatus 100 may include an imaging optical system that forms a two-dimensional image of the user on the light-receiving surface of the image sensor 30. An optical axis of the imaging optical system is substantially perpendicular to the light-receiving surface of the image sensor 30. The imaging optical system may include a zoom lens. As a position of the zoom lens changes, magnification power for the two-dimensional image of the user changes, and accordingly the resolution of the two-dimensional image on the image sensor 30 changes. Even if the user is distant, therefore, a part to be measured can be magnified and closely observed.

The biometric apparatus 100 may include, between the user and the image sensor 30, a bandpass filter that passes only light within or around a wavelength band used by the light source 20. As a result, an effect of a disturbance component such as ambient light can be reduced. The bandpass filter is achieved by a multilayer filter or an absorption filter. The bandwidth of the bandpass filter may have a width of 20 to 100 nm in consideration of a band shift dependent on the temperature of the light source 20 and grazing incident on the bandpass filter.

The biometric apparatus 100 may include a polarizer between the light source 20 and the user and between the image sensor 30 and the user. In this case, a polarizing direction of the polarizer for the light source 20 and a polarizing direction of the polarizer for the image sensor 30 are in a relationship of crossed Nicols. As a result, a specular reflection component, that is, a component whose angle of incidence and angle of reflection are the same, of the surface reflection component I1 can be prevented from reaching the image sensor 30. That is, the amount of light of the surface reflection component I1 reaching the image sensor 30 can be reduced.

2. Time-Resolved Imaging

As described above, the biometric apparatus 100 according to the present embodiment can separately detect the surface reflection component I1 and the internal scattering component I2 radiated onto a target part. Such imaging will be referred to as "time-resolved imaging" herein.

An example of the operation of the biometric apparatus 100 according to the present embodiment will be described hereinafter.

As illustrated in FIG. 1B, when the light source 20 radiates a light pulse onto the user, the surface reflection component I1 and the internal scattering component I2 are generated. Parts of the surface reflection component I1 and the internal scattering component I2 reach the image sensor 30. The internal scattering component I2 passes through the user while being emitted from the light source 20 and reaching the image sensor 30. That is, an optical path of the internal scattering component I2 is longer than an optical path of the surface reflection component I1. The internal scattering component I2, therefore, generally reaches the image sensor 30 later than the surface reflection component I1 does.

The surface reflection component I1 can be detected, for example, by performing the following operation.

Figure 7:
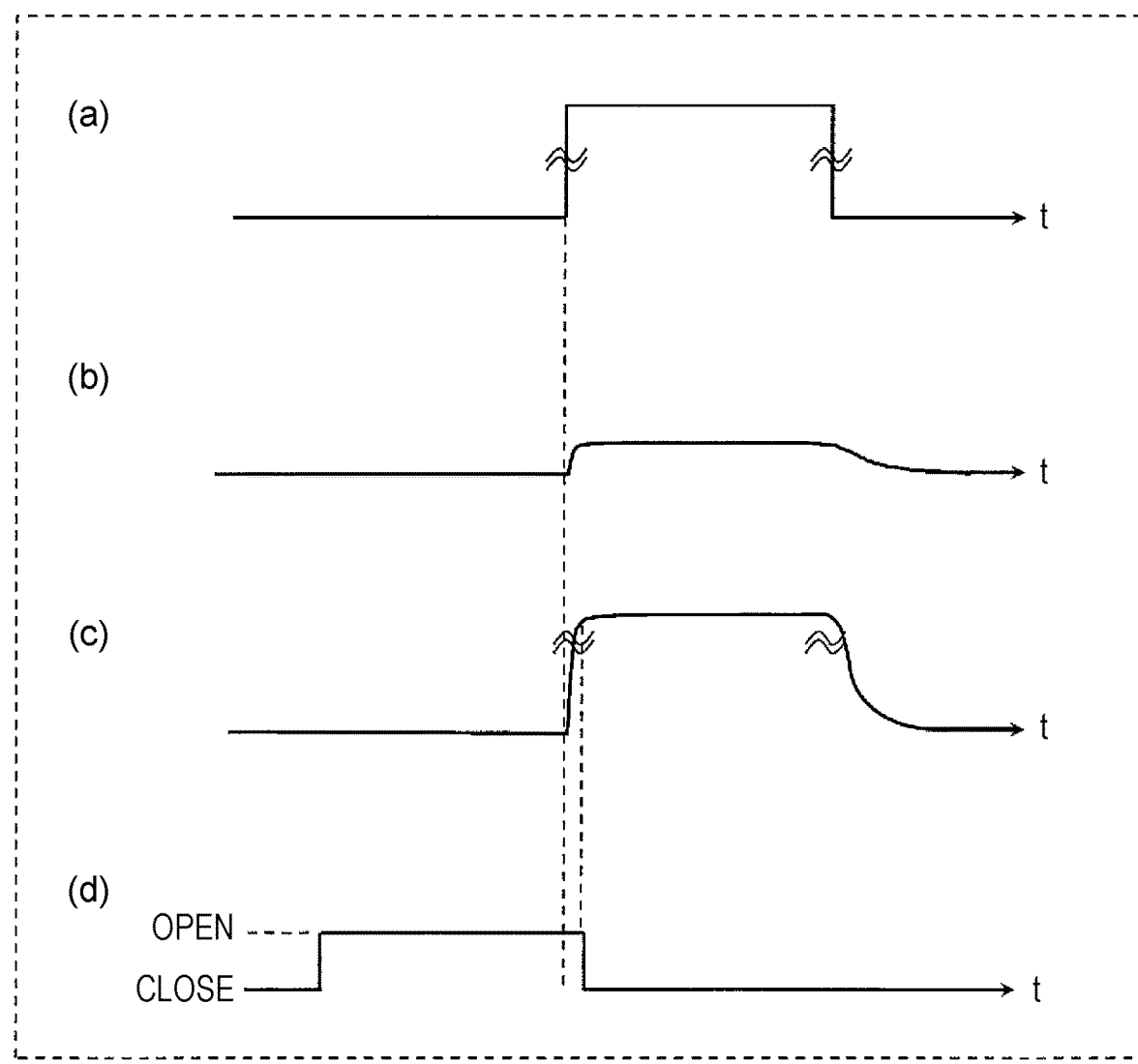
FIG. 7 is a diagram illustrating an example of a light signal at a time when the light source emits a rectangular light pulse and light returning from a user reaches the image sensor.

FIG. 7 is a diagram illustrating an example of a light signal at a time when the light source 20 emits a rectangular light pulse and light returning from the user reaches the image sensor 30. Horizontal axes in portions (a) to (d) of FIG. 7 represent time (t). Vertical axes in portions (a) to (c) of FIG. 7 represent intensity, and a vertical axis in portion (d) of FIG. 7 represents an open state or a close state of the electronic shutter. Portion (a) of FIG. 7 illustrates the surface reflection component I1. Portion (b) of FIG. 7 illustrates the internal scattering component I2. Portion (c) of FIG. 7 illustrates a combined component of the surface reflection component I1 illustrated in portion (a) of FIG. 7 and the internal scattering component I2 illustrated in portion (b) of FIG. 7. Portion (d) of FIG. 7 illustrates a shutter timing for obtaining the surface reflection component I1 from the user.

As illustrated in portion (d) of FIG. 7, by opening the electronic shutter, components of reflected light incident early on the image sensor 30 can be efficiently collected. The components incident early have been hardly scattered in a target part and includes surface information regarding the target part. A period in which light is actually accumulated is a short period of time at a leading edge of a pulse wave, but the electronic shutter need not necessarily open only in this period of time. As illustrated in portion (d) of FIG. 7, the electronic shutter may open before a leading edge of a pulse wave reaches the image sensor 30. In the example illustrated in portion (d) of FIG. 7, a leading edge of a reflected light pulse is detected immediately before an exposure period ends. When such shutter control is employed, an expensive image sensor capable of performing exposure in order of picoseconds need not be used. The biometric apparatus 100 according to the present embodiment can be achieved by a reasonable image sensor 30.

In the example illustrated in FIG. 7, the light source 20 radiates a rectangular pulse wave. At this time, pulse width need not be on the order of picoseconds but may be several nanoseconds. A reasonable light source, therefore, can be used.

Although only a leading edge of a reflected light pulse is detected in this example, the detection method used is not limited to this. For example, the exposure period may include a period from an end of a rising period to a beginning of a falling period. With this detection method, too, image data indicating the appearance of the user's face can be obtained.

Next, an example of a method for detecting the internal scattering component I2 will be described.

Figure 8:
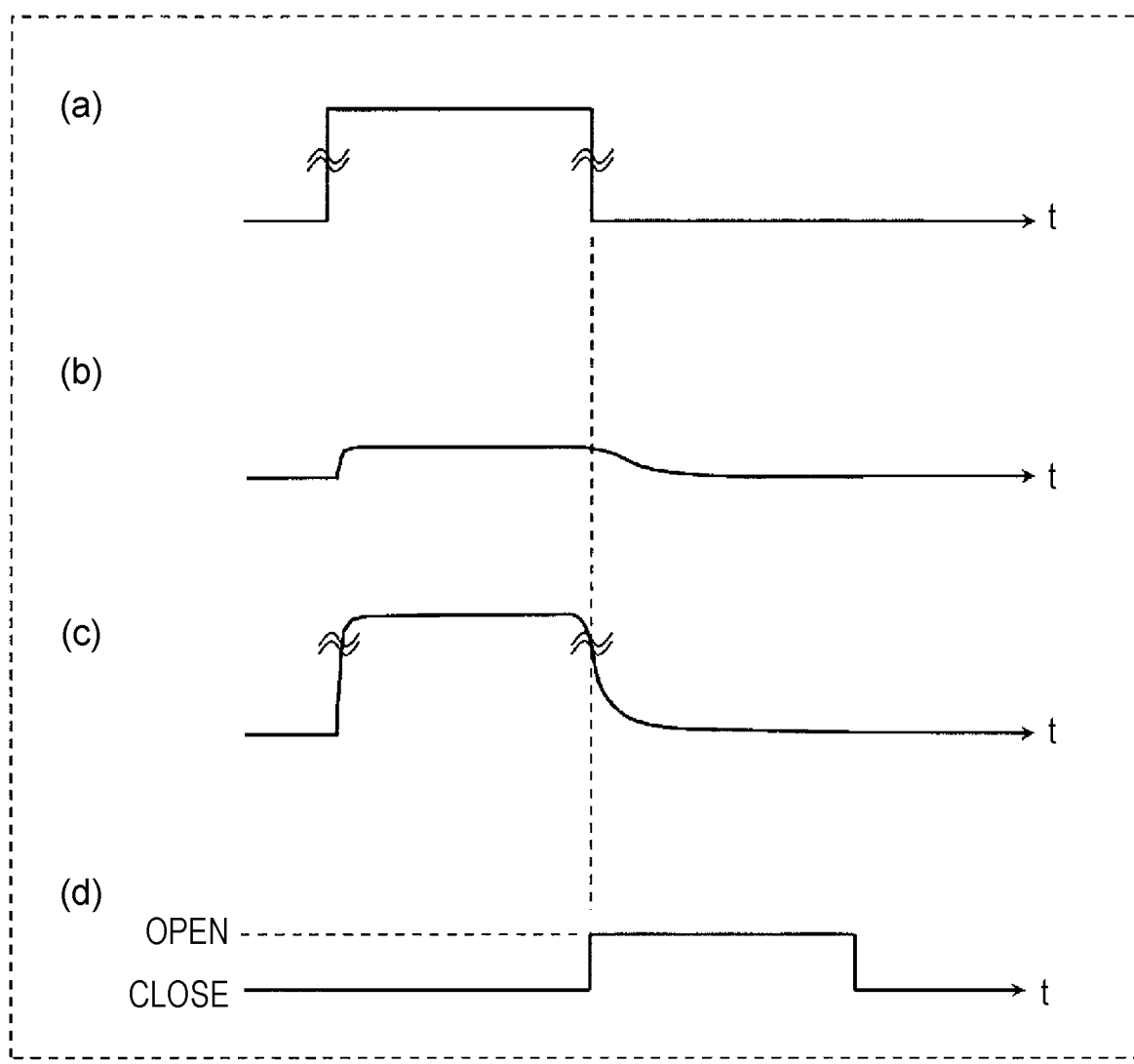
FIG. 8 is a diagram illustrating another example of the light signal at the time when the light source emits a rectangular light pulse and light returning from a user reaches the image sensor.

FIG. 8 is a diagram illustrating another example of the light signal at the time when the light source 20 emits a rectangular light pulse and light returning from the user reaches the image sensor 30. Portions (a) to (c) of FIG. 8 illustrate the same temporal changes as in portions (a) to (c) of FIG. 7. Portion (d) of FIG. 8 illustrates a shutter timing for obtaining the internal scattering component I2.

As illustrated in portion (a) of FIG. 8, the surface reflection component I1 remains rectangular. As illustrated in portion (b) of FIG. 8, however, since the internal scattering component I2 is the sum of light beams having various optical path lengths, a trailing edge of the light pulse gradually attenuates. That is, a failing period of the internal scattering component I2 is longer than a falling period of the surface reflection component I1. In order to extract the internal scattering component I2 from a light signal illustrated in portion (c) of FIG. 8 as much as possible, the electronic shutter begins to accumulate charge after a trailing edge of the surface reflection component I1 as illustrated in portion (d) of FIG. 8. "After the trailing edge of the surface reflection component I1" refers to when the surface reflection component I1 has begun to fall and later points in time. The control circuit 60 adjusts the shutter timing. As described above, the biometric apparatus 100 according to the present embodiment separately detects the surface reflection component I1 and the internal scattering component I2. Emission pulse width and shutter width, therefore, may be set as desired. Unlike with a conventional method employing a streak camera, therefore, the internal scattering component I2 can be obtained with a simple configuration, thereby reducing cost.

In order to perform an operation illustrated in portion (d) of FIG. 8, the control circuit 60 causes the image sensor 30 to detect at least some of components of the reflected light pulse in a failing period and output a signal indicating a two-dimensional image of the user. In the present embodiment, a signal output from the image sensor 30 can include a signal indicating the amount of light of the at least some of the components of the reflected light pulse in the falling period.

In portion (a) of FIG. 8, the trailing edge of the surface reflection component I1 vertically falls. In other words, time taken until the surface reflection component I1 finishes falling after beginning to fall is zero. In practice, however, a light pulse emitted by the light source 20 might not be completely rectangular, the surface of the user might be slightly uneven, or the trailing edge of the surface reflection component I1 might not vertically fall due to scattering inside the outer layer of the skin. In addition, since the user is an opaque object, the amount of light of the surface reflection component I1 is considerably larger than that of the internal scattering component I2. Even when the trailing edge of the surface reflection component I1 slightly protrudes from a vertical falling position, therefore, the internal scattering component I2 might be buried. Furthermore, a lag might be caused by movement of electrons during a reading period of the electronic shutter. For this reason, ideal binary reading illustrated in portion (d) of FIG. 8 might not be achieved. In this case, the control circuit 60 may slightly delay the shutter timing of the electronic shutter to a time point immediately after the surface reflection component I1 begins to fall. For example, the shutter timing may be delayed by 0.5 to 5 ns. The control circuit 60 may adjust an emission timing of the light source 20 instead of adjusting a shutter timing of the electronic shutter. In other words, the control circuit 60 may adjust a time difference between a shutter timing of the electronic shutter and an emission timing of the light source 20. If a shutter timing is delayed too much, the internal scattering component I2, which is small from the start, is further reduced. A shutter timing, therefore, may stay around the trailing edge of the surface reflection component I1. As described above, since a lag due to scattering inside the forehead is 4 ns, the shutter timing can be delayed by about 4 ns at maximum.

Light pulses emitted from the light source 20 may be exposed with shutter timings having the same time difference, and signals may be accumulated. In this case, the amount of light of the internal scattering component I2 detected increases.

An offset component may be estimated by performing imaging with the same exposure period without the light source 20 emitting light instead of, or in addition to, providing a bandpass filter between the user and the image sensor 30. The estimated offset component is removed from signals detected by each pixel of the image sensor 30 through subtraction. As a result, an effect of a dark current component and/or disturbance light generated on the image sensor 30 can be removed.

Next, an example of a method for detecting the surface reflection component I1 and the internal scattering component I2 in each frame will be described.

Figure 9A:
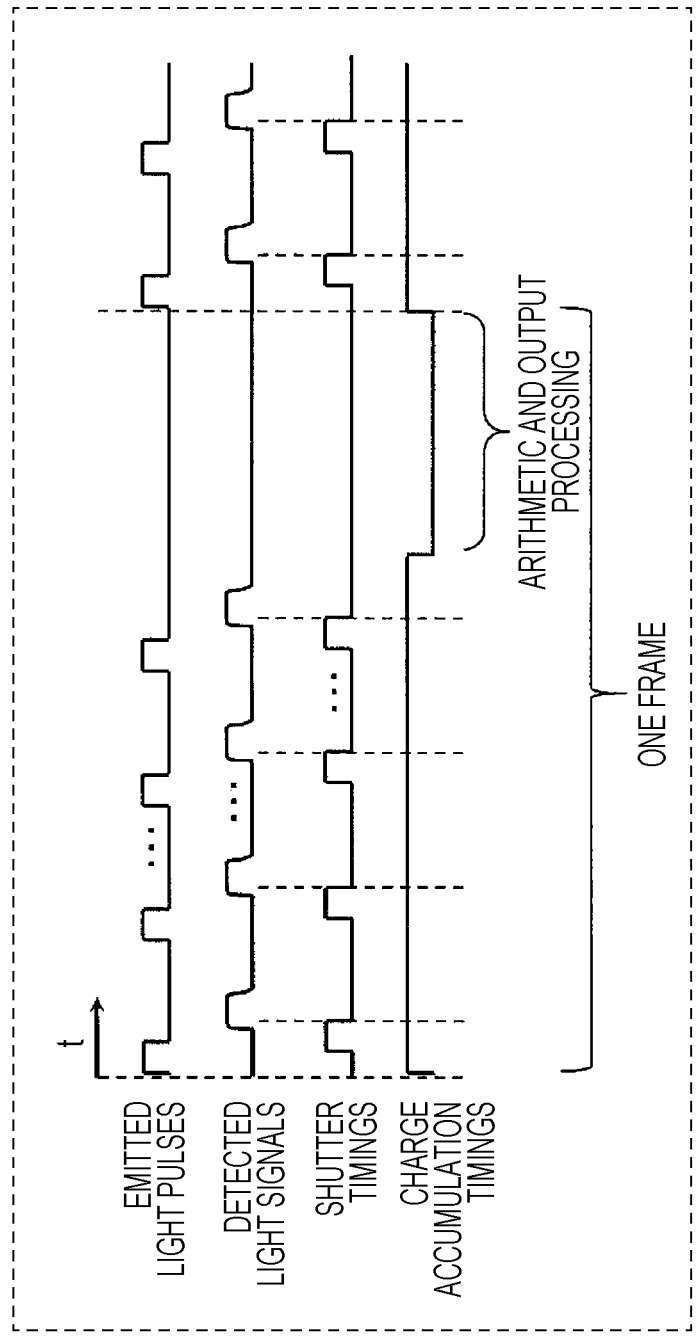
FIG. 9A is a diagram illustrating an example of a timing chart at a time when a surface reflection component is detected.

FIG. 9A illustrates an example of a timing chart at a time when the surface reflection component I1 is detected. As illustrated in FIG. 9A, for example, the electronic shutter may open before a light pulse reaches the image sensor 30 and close before a trailing edge of the light pulse reaches the image sensor 30 in order to detect the surface reflection component I1. By controlling the electronic shutter in this manner, mixing of the internal scattering component I2 can be suppressed and the percentage of light that passes near the surface of the user can be increased. In particular, a timing at which the electronic shutter closes may be immediately after the light reaches the image sensor 30. In this case, signals in which the percentage of the surface reflection component I1 whose optical path is relatively short is increased can be detected. In another method for obtaining the surface reflection component I1, the image sensor 30 may obtain the entirety of a light pulse or the light source 20 may radiate continuous light and the image sensor 30 may detect the continuous light.

FIG. 9B illustrates an example of a timing chart at a time when the internal scattering component I2 is detected. In this example, the electronic shutter opens after a trailing edge of a light pulse begins to reach the image sensor 30. As a result of this control, a signal of the internal scattering component I2 can be obtained.

When time-resolved imaging is performed with the same image sensor as in the present embodiment, temporal and spatial deviation is unlikely to occur. When signals of both the surface reflection component I1 and the internal scattering component I2 are to be obtained with the same image sensor, a component to be obtained may be switched frame by frame as illustrated in FIGS. 9A and 9B. Alternatively, as described with reference to FIGS. 5 and 6A, a component to be obtained may alternate at high speed between the surface reflection component I1 and the internal scattering component I2 in each frame. In this case, a detection time difference between the surface reflection component I1 and the internal scattering component I2 can be reduced.

Furthermore, signals of the surface reflection component I1 and the internal scattering component I2 may each be obtained using light of two wavelengths. When the surface reflection component I1 and the internal scattering component I2 are each obtained with two wavelengths, for example, a method in which four types of accumulation of charge are sequentially performed at high speed in each frame can be used as described with reference to FIGS. 4A to 5. With this method, temporal deviation of detected signals can be reduced.

3. Example of Detection of Changes in Cerebral Blood Flow

Next, an example of a method for detecting changes in cerebral blood flow of the user will be described.

Figure 10A:
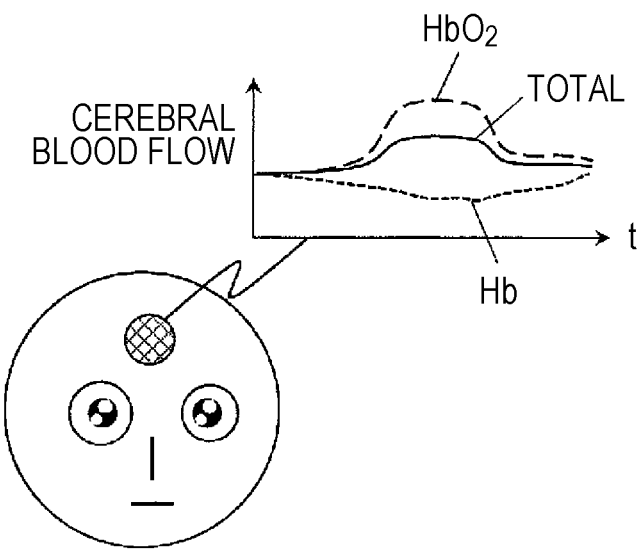
FIG. 10A is a diagram schematically illustrating an example of temporal changes in cerebral blood flow.

FIG. 10A is a diagram schematically illustrating an example of temporal changes in cerebral blood flow. As illustrated in FIG. 10A, a target part of the user is irradiated with light from the light source 20, and returning light is detected. In this case, the surface reflection component I1 is considerably larger than the internal scattering component I2. With the above-described shutter adjustment, however, only the internal scattering component I2 can be extracted. A graph of FIG. 10A illustrates an example of temporal changes in the concentration of oxygenated hemoglobin ($HbO_2$) and deoxygenated hemoglobin (Hb) in cerebral blood flow. The internal scattering component I2 in this example is obtained using light of two wavelengths. The concentration illustrated in FIG. 10A indicates the amount of change from an amount in a normal state. The amount of change is calculated by the signal processing circuit 70 on the basis of a light intensity signal. Cerebral blood flow changes in accordance with a brain activity state such as the normal state, a concentrating state, or a relaxed state. Depending on a position in the target part, for example, brain activity, that is, an absorption coefficient or scattering coefficient, differs. Temporal changes in cerebral blood flow are therefore measured at the same position in the target part of the user. When temporal changes in brain activity are detected, the state of the user can be estimated from relative temporal changes in cerebral blood flow even if the absolute amount of cerebral blood flow is unknown.

Figure 10B:
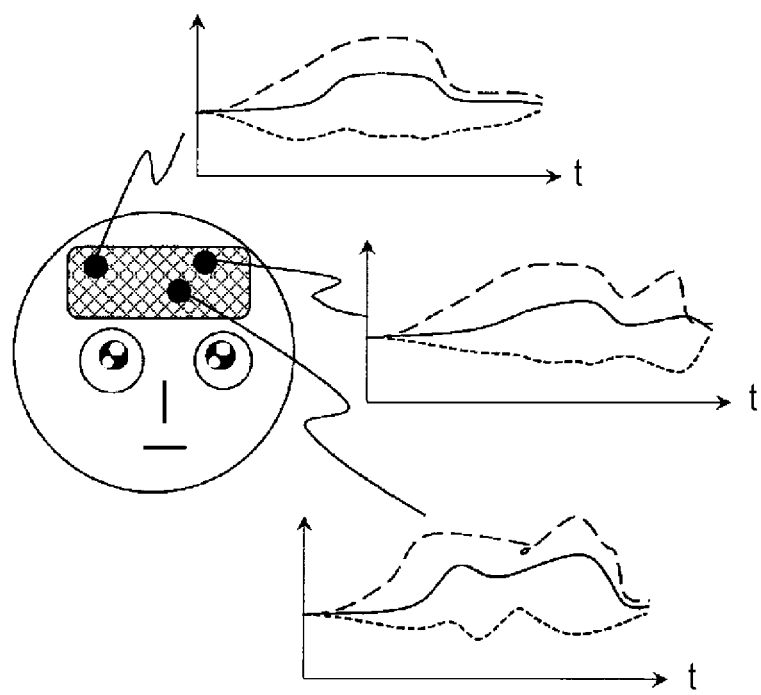
FIG. 10B is a diagram schematically illustrating an example of a case where measurement is simultaneously performed at different positions in a target part of the user.

FIG. 10B is a diagram schematically illustrating an example of a case where measurement is simultaneously performed at different positions in a target part of the user. Because a two-dimensional area is imaged in this example, the two-dimensional distribution of cerebral blood flow can be obtained. In this case, a radiation pattern of the light source 20 may be, for example, uniform intensity distribution, dot-like distribution, or donut-shaped distribution. When radiation is performed with uniform intensity distribution, irradiation positions in the target part need not be adjusted or can be simplified. With the radiation employing uniform intensity distribution, light is incident on the target part of the user from various angles. A signal detected by the image sensor 30 can therefore be increased. Furthermore, measurement can be performed at any position within an irradiation area. With partial radiation such as radiation employing dot-like distribution or donut-shaped distribution, an effect of the surface reflection component I1 can be reduced just by moving the target part from an irradiation area.

Figure 11A:
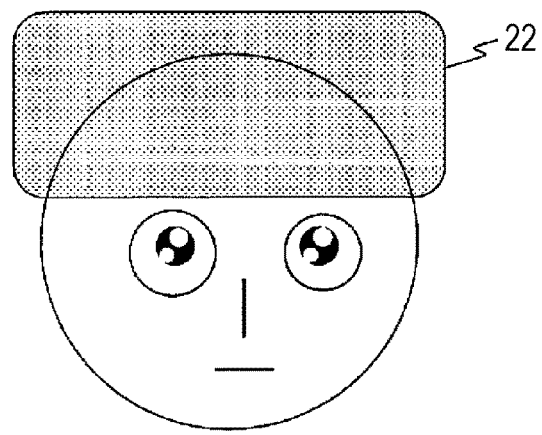
FIG. 11A is a diagram schematically illustrating an example of an irradiation area with light.

FIG. 11A is a diagram schematically illustrating an example of an irradiation area 22 with light. In noncontact measurement of cerebral blood flow, the amount of light detected attenuates in inverse proportion to a square of distance from the biometric apparatus 100 to the target part. Signals from each pixel detected by the image sensor 30 may therefore be increased by adding up signals from neighboring pixels. In doing so, the total number of pulses can be reduced while maintaining the S/N ratio. As a result, a frame rate improves. FIG. 11A illustrates an example in which light is radiated onto only the user's head. When a face image of the user is obtained using the same light, the user's face is included in an irradiation area. When a face image is obtained using different light, the light source 20 need not radiate light onto an area other than the head.

Figure 11B:
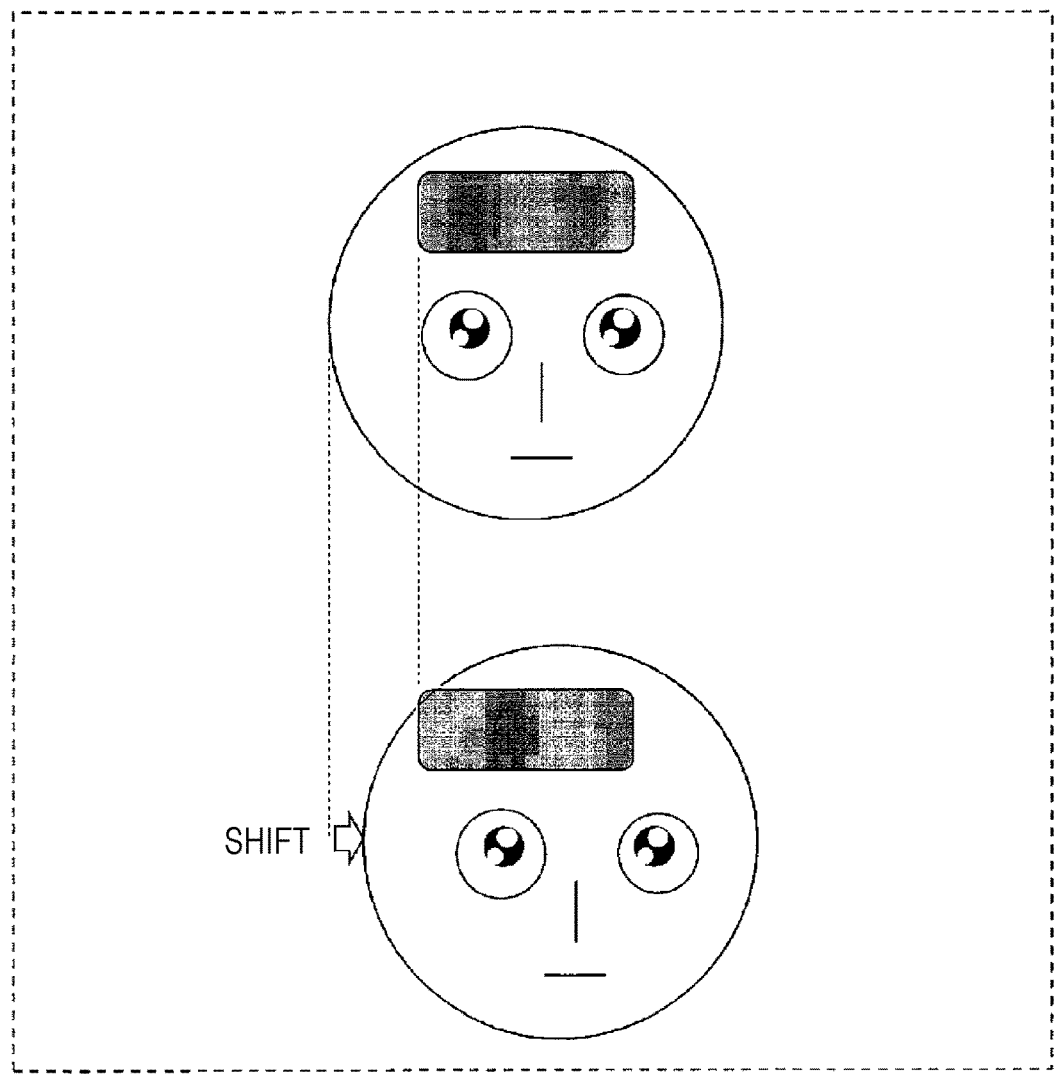
FIG. 11B is a diagram schematically illustrating changes in a signal at a time when a target part of the user has laterally shifted.

FIG. 11B is a diagram schematically illustrating changes in a signal at a time when a target part of the user has laterally shifted. As described above, changes in brain activity are read by detecting a difference between cerebral blood flow at a time when brain activity has changed from the normal state and cerebral blood flow in the normal state. When an image sensor 30 including photoelectronic conversion elements arranged in two dimensions is used, two-dimensional brain activity distribution can be obtained as illustrated in an upper part of FIG. 11B. In this case, a part in which brain activity is significant can be detected from relative intensity distribution in two-dimensional distribution without obtaining signals in the normal state in advance. Since noncontact measurement is performed in the present embodiment, a position of the target part might change during the measurement as illustrated in FIG. 11B. This can occur when, for example, the user slightly moves due to respiration. In general, two-dimensional distribution of cerebral blood flow does not sharply changes in a short period of time. Deviation of the target part can therefore be corrected through, for example, pattern matching of detected two-dimensional distribution between frames. Alternatively, in the case of periodical movement such as respiration, only a frequency component of the periodical movement may be extracted and corrected or removed. The number of target parts need not be one and may be two or more. Two or more target parts may be, for example, left and light parts or dot-like distribution of 2×6 matrices.

4. Estimation of State of User

Next, an example of a method for estimating the state of the user using the biometric apparatus 100 will be described. The biometric apparatus 100 can be used in a system that provides video content or sound content, for example, over a network such as the Internet. Such a system can include, for example, a server managed by an organization and one of various computers such as personal computers (PCs), smartphones, and tablets owned by the user. The server 200 illustrated in FIG. 1B may be the server included in the system.

Users can use such a system. The users use the biometric apparatus 100. The users can view, through the stimulation device 10 using a computer such as a smartphone, content delivered from the server, such as an application, a moving image, or a video game. The biometric apparatus 100 may be incorporated into or connected to from the computer owned by the user.

4-1. Determination of Degree of Interest of User

An example of a method for determining a degree of interest of the user will be described. In this example, image data indicating the appearance of the user's face and image data indicating the state of cerebral blood flow of the user are repeatedly generated using the above-described method while the user is viewing video content displayed on a display. In this example, as described with reference to FIGS. 4A to 5, a total of four types of image data based on the surface reflection component I1 and the internal scattering component I2 corresponding to light of two wavelengths are generated in each frame using the light of two wavelengths. Two types of image data based on the surface reflection component I1 will be referred to as "first image data", and two types of image data based on the internal scattering component I2 will be referred to as "second image data" hereinafter. The signal processing circuit 70 detects changes in the user's line of sight on the basis of temporal changes in the first image data and changes in brain activity of the user on the basis of the second image data. The signal processing circuit 70 identifies a timing at which the degree of interest of the user is high and a point at which the user is gazing at the timing on the basis of results of the detection. As a result, a part of the video content in which the user is particularly interested can be estimated.

Figure 12A:
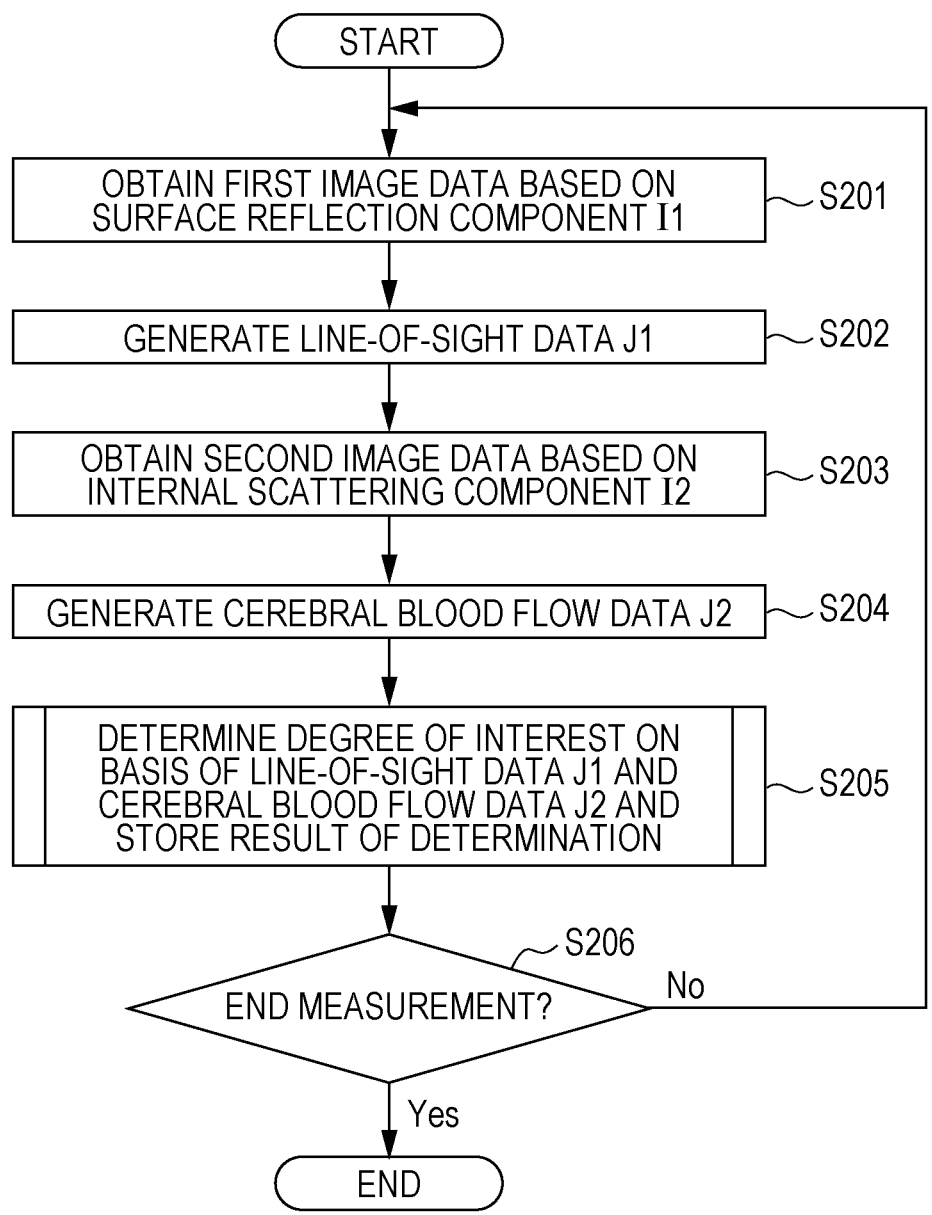
FIG. 12A is a flowchart illustrating an example of a process for determining a degree of interest.

FIG. 12A is a flowchart illustrating an example of a process for determining a degree of interest according to the present embodiment. In this example, the signal processing circuit 70 performs steps S201 to S206 illustrated in FIG. 12A for each frame.

In step S201, the signal processing circuit 70 obtains the first image data based on the surface reflection component I1. As described above, the first image data is repeatedly output to the image sensor 30 at the first frame rate.

In step S202, the signal processing circuit 70 generates line-of-sight data J1 on the basis of the first image data. The line-of-sight data indicates a direction of the user's line of sight. The line-of-sight data J1 can indicate, for example, coordinates of the center of the user's pupil. The coordinates of the center of the user's pupil can be calculated, for example, from a positional relationship between a position of the center of the user's pupil and Purkinje images, which are corneal reflections, using a known corneal reflection method. There are various corneal reflection methods that can be used to calculate a position of an eyeball. As disclosed in Ashit Talukder et al., "A Real-time Non-Intrusive Eyetracking and Gaze-Point Determination for Human-Computer Interaction and Biomedicine", SPIE Defense and Security Symposium, Optical Patter Recognition XV, Orlando, FL, Apr. 12-16, 2004, for example, a method in which the amount of movement of the center of the pupil in a horizontal direction and a vertical direction viewed from a camera is projected onto a surface of a display may be used. In the present embodiment, the first image data includes image data corresponding to light having a wavelength shorter than 805 nm and image data corresponding to light having a wavelength longer than 805 nm. The line-of-sight data J1 may be generated on the basis of only one of the two pieces of image data or both the pieces of image data.

In step S203, the signal processing circuit 70 obtains the second image data based on the surface reflection component I1. As described above, the second image data is repeatedly output from the image sensor 30 at the second frame rate.

In step S204, the signal processing circuit 70 generates cerebral blood flow data J2 on the basis of the second image data. The cerebral blood flow data J2 indicates the state of cerebral blood flow of the user. The cerebral blood flow data J2 can be, for example, data indicating the concentration of oxygenated hemoglobin ($HbO_2$) and deoxygenated hemoglobin (Hb) in cerebral blood flow. In the present embodiment, the second image data includes image data corresponding to light having a wavelength shorter than 805 nm and image data corresponding to light having a wavelength longer than 805 nm. As described above, with light having a wavelength longer than 805 nm, the absorbance of $HbO_2$ is higher than that of Hb. Conversely, with light having a wavelength shorter than 805 nm, the absorbance of Hb is higher than that of $HbO_2$. By solving predetermined simultaneous equations using values of the amount of light detected by each pixel, therefore, the amount of change in the concentration of $HbO_2$ and Hb in blood from reference values can be obtained. Data regarding the amount of change can be used as the cerebral blood flow data J2. Alternatively, data regarding the concentration of either $HbO_2$ or Hb may be used as the cerebral blood flow data J2.

In step S205, the signal processing circuit 70 determines the degree of interest of the user on the basis of the line-of-sight data J1 and the cerebral blood flow data J2 and stores data indicating a result of the determination. Details of the determination will be described later with reference to FIG. 12B.

The signal processing circuit 70 repeats steps S201 to S205 until receiving an instruction to end the measurement in step S206.

Figure 12B:
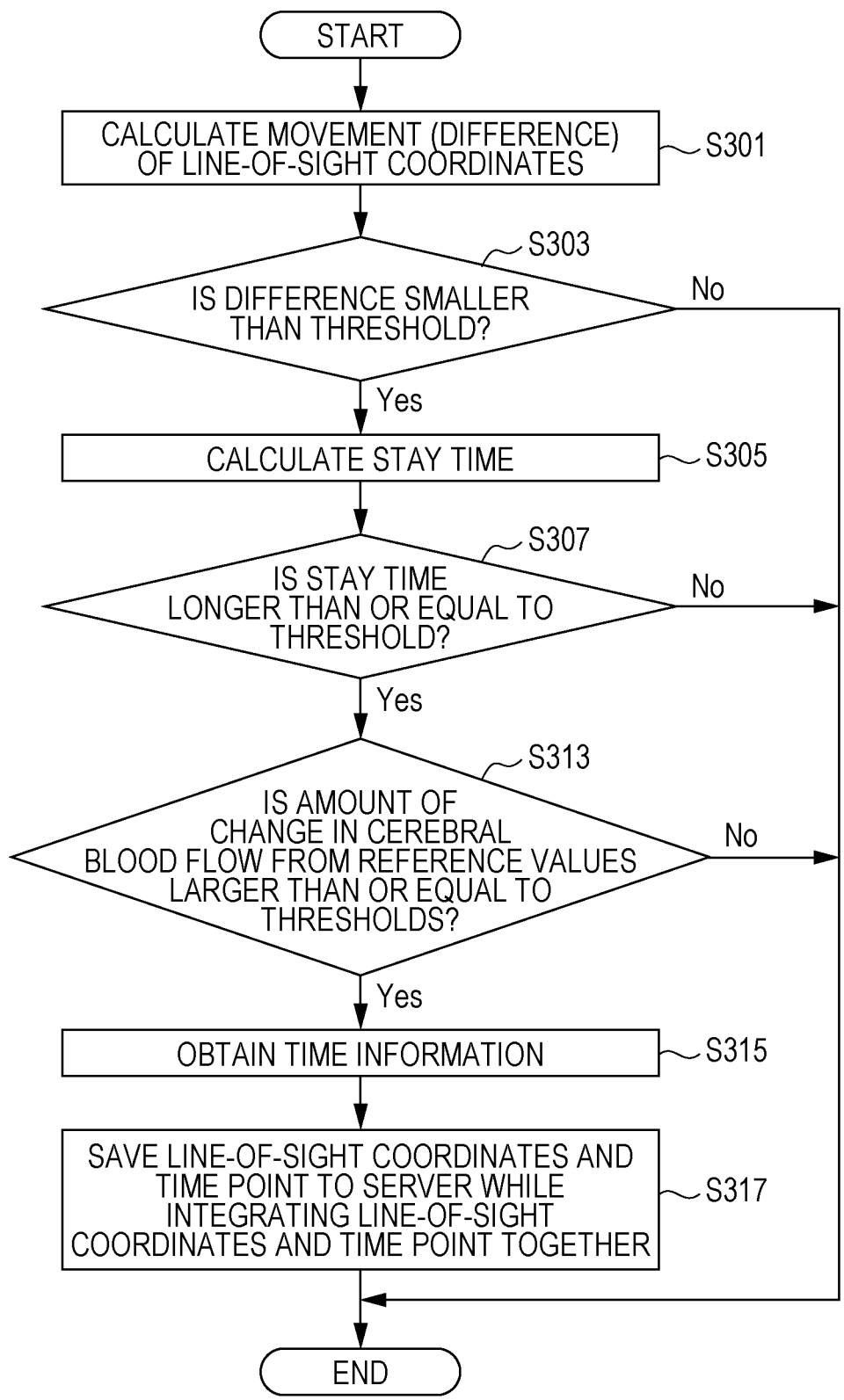
FIG. 12B is a flowchart illustrating an example of a process performed in step S205 illustrated in FIG. 12A.

FIG. 12B is a flowchart illustrating a specific example of a process performed in step S205. The signal processing circuit 70 performs steps S301 to S317 illustrated in FIG. 12B.

In step S301, the signal processing circuit 70 calculates movement of line-of-sight coordinates on the basis of the line-of-sight data J1. The movement of line-of-sight coordinates can be, for example, a difference between line-of-sight coordinates and line-of-sight coordinates at a timing of previous sampling.

In step S303, the signal processing circuit 70 determines whether the difference is smaller than a threshold. For example, the signal processing circuit 70 determines, while defining a horizontal direction as an x-axis direction and a vertical direction as y-axis direction, whether the difference in the line-of-sight coordinates is smaller than a certain threshold, namely ±10, for example, for the X and Y coordinates.

If the difference in the line-of-sight coordinates is larger than or equal to the threshold, the signal processing circuit 70 can determine that the user's line of sight has moved. In this case, the process proceeds to step S206 while omitting later steps. If the difference in the line-of-sight coordinates is smaller than the threshold, on the other hand, the process proceeds to step S305.

In step S305, the signal processing circuit 70 calculates stay time at the line-of-sight coordinates. The stay time can be calculated by adding a time interval of sampling to stay time calculated at the timing of previous sampling.

In step S307, the signal processing circuit 70 determines whether the calculated stay time is longer than or equal to a certain threshold. If the stay time is shorter than the threshold, the process proceeds to step S206 while omitting later steps. If the stay time is longer than or equal to the threshold, on the other hand, the signal processing circuit 70 determines that the user is gazing the line-of-sight coordinates, and the process proceeds to step S313.

In step S313, the signal processing circuit 70 determines, on the basis of the cerebral blood flow data J2 generated in step S204, whether the amount of change in cerebral blood flow from reference values is larger than or equal to thresholds. For example, a threshold for the amount of change from a reference value can be set in advance for each of the concentration of oxygenated hemoglobin and the concentration of deoxygenated hemoglobin in cerebral blood flow. The signal processing circuit 70 determines, for each of the concentration of oxygenated hemoglobin and the concentration of deoxygenated hemoglobin in cerebral blood flow, whether the amount of change from the corresponding reference value is larger than or equal to the corresponding threshold. If a result of the determination is No, it is estimated that the degree of interest of the user is low, and the process proceeds to step S206 while omitting later steps. If the result of the determination is Yes, it is estimated that the degree of interest of the user is high, and the process proceeds to step S315.

Figure 13:
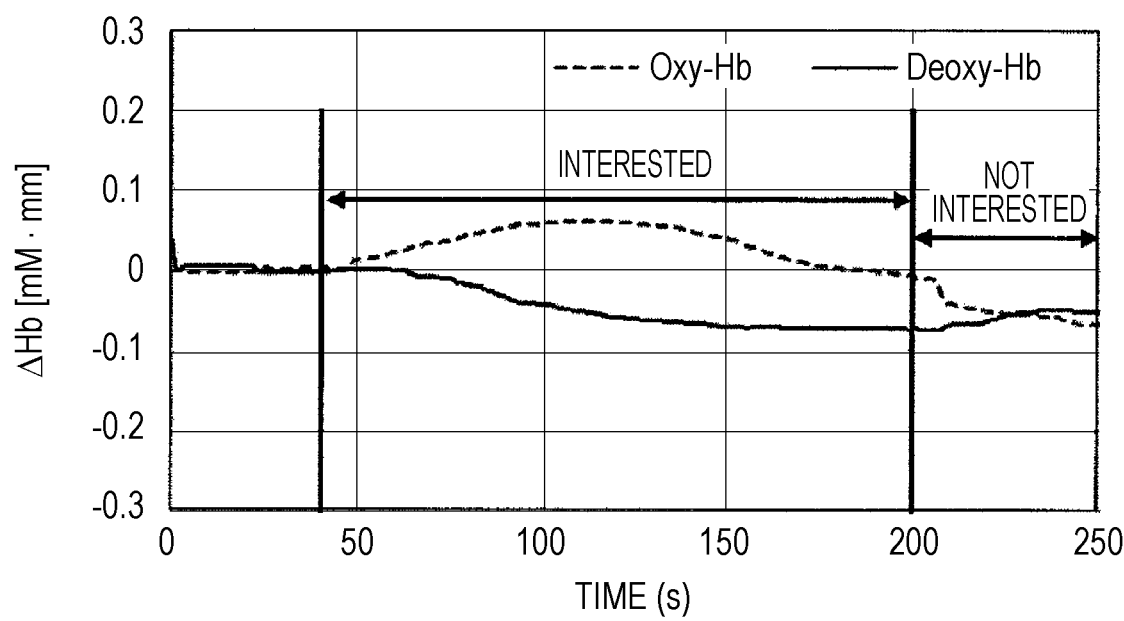
FIG. 13 is a diagram illustrating an example of temporal changes in the concentration of oxygenated hemoglobin and deoxygenated hemoglobin in cerebral blood flow.

Now, an example of the determination based on the cerebral blood flow data J2 will be described with reference to FIG. 13. FIG. 13 illustrates an example of temporal changes in the concentration of oxygenated hemoglobin (Oxy-Hb) and deoxygenated hemoglobin (Deoxy-Hb) in cerebral blood flow. A horizontal axis represents time, and a vertical axis represents the amount of change in concentration from the corresponding reference value. Data was obtained by measuring frontal lobe blood flow using the biometric apparatus 100 according to the present embodiment with the user's line of sight fixed. An experiment in which an object in which the user was interested and an object in which the user was not interested were sequentially presented at an end of the user's line of sight, which was fixed. It can be seen from results illustrated in FIG. 13 that trend of temporal changes in cerebral blood flow was different between when the user was looking at the object in which he/she was interested and when the user was looking at the object in which he/she was not interested. According to the results illustrated in FIG. 13, the concentration of Oxy-Hb tended to increase and the concentration of Deoxy-Hb tended to decrease when the user was looking at the object in which he/she was interested. The degree of interest of the user can thus be estimated on the basis of the amount of change in the concentration of Oxy-Hb and/or the concentration of Deoxy-Hb from the corresponding reference values.

Although presence or absence of the user's interest is estimated in the present embodiment, another psychological state or physical state, such as fear, sleepiness, pleasure, or fatigue, can be estimated in the same manner. According to Hirokazu Doi et al., "NIRS as a tool for assaying emotional function in the prefrontal cortex", Front Hum Neurosci. 2013, for example, Oxy-Hb increases in reaction to an unpleasant stimulus, and especially Oxy-Hb in the right prefrontal cortex (PFC) increases due to anxiety caused by a fear stimulus. It has also been reported that right Oxy-Hb increases in reaction to a cognitive load of mental arithmetic tasks and Oxy-Hb in cerebral blood flow in the orbitofrontal cortex (OFC) increases when a subject sees a smile. Masashi Suda et al., "Decreased cortical reactivity underlies subjective daytime light sleepiness in healthy subjects: a multichannel near-infrared spectroscopy study", Neurosci Res. 60: 319-326, 2008 discloses that as a subject who is performing language fluency tasks becomes more aware of his/her own sleepiness, Oxy-Hb in the dorsolateral prefrontal cortex (DLPFC) decreases, or increases less than when the subject is not feeling sleepy. Masashi Suda et al., "Subjective feeling of psychological fatigue is related to decreased reactivity in ventrolateral prefrontal cortex", Brain Res. 1252 152-160, 2009 discloses, as a result of examination of activation of the frontal lobe through language fluency tasks using near-infrared spectroscopy (NIRS), that as a subject becomes more aware of his/her own fatigue, an increase in Oxy-Hb in the left and right ventrolateral prefrontal cortex (VLPFC) becomes smaller. Furthermore, Mototaka Yoshioka et al., "Brain signal pattern of engrossed subjects using near infrared spectroscopy (NIRS) and its application to TV commercial evaluation", IJCNN 2012: 1-6 discloses that Oxy-Hb in the frontal cortex decreases when a subject is absorbed in tasks and concentrating. The biometric method according to the present embodiment, therefore, can be used to estimate another psychological or physical state regardless of the degree of interest of the user.

FIG. 12B will be referred to again. If a result of step S313 is Yes, the process proceeds to step S315. In step S315, the signal processing circuit 70 obtains current time information regarding content that the user is viewing.

In step S317, the signal processing circuit 70 integrates current line-of-sight coordinates and present time together and saves the line-of-sight coordinates and the time point to the server 200. As a result, a position of a target in the content that the user is viewing and the present time are saved while being associated with each other.

Figure 12C:
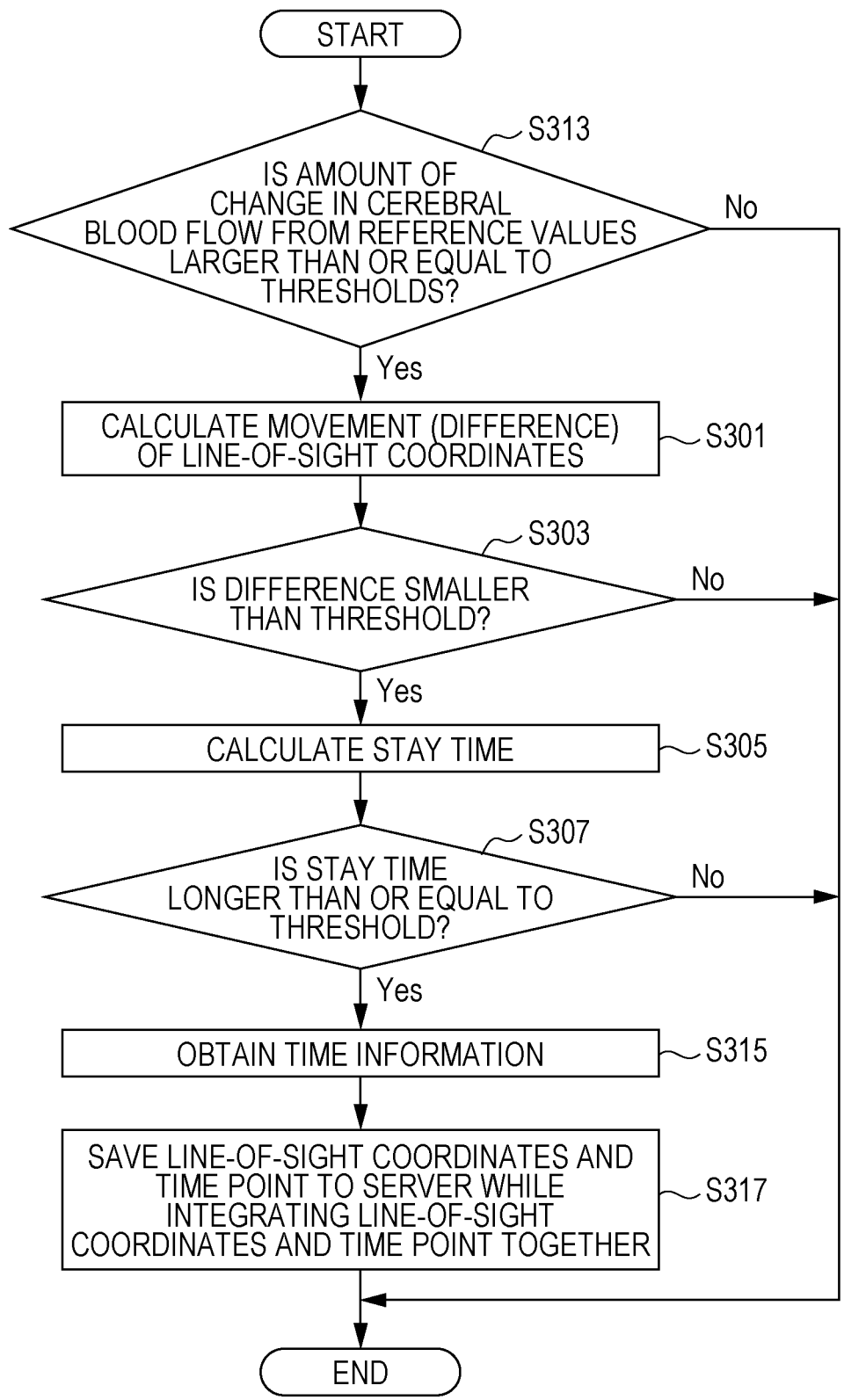
FIG. 12C is a flowchart illustrating another example of the process performed in step S205 illustrated in FIG. 12A.

The process illustrated in FIG. 12B is an example, and may be modified in various ways. For example, as illustrated in FIG. 12C, order of steps S301 to S307 and step S313 may be switched. In an example illustrated in FIG. 12C, first, whether the amount of change in cerebral blood flow from the reference values is larger than or equal to the thresholds is determined. If a result of the determination is No, the process proceeds to step S206 while omitting later steps. Only if the result of the determination is Yes, the process proceeds to step S301 and later steps. This operation, too, can produce the same effects. In the example illustrated in FIG. 12A, step S205 is performed in real-time while the user is viewing the content. Alternatively, step S205 may be performed after steps S201 to S204 during viewing are all completed. In this case, the signal processing circuit 70 may repeatedly perform the process illustrated in FIG. 12A or 12B at certain sampling intervals.

As a result of the above operation, a part of content that the user is viewing in which the user is interested can be identified. The server 200 may accumulate data in which line-of-sight coordinates and time points are associated with each other for each user and for each piece of content. The control circuit 60 of the biometric apparatus 100 owned by each user may change a stimulus or content to be presented to the user on the basis of the data accumulated in the server 200.

4-2. First Applied Process after Determination of Degree of Interest of User

Next, an example of a process performed after a determination of the degree of interest of the user will be described.

Figure 14A:
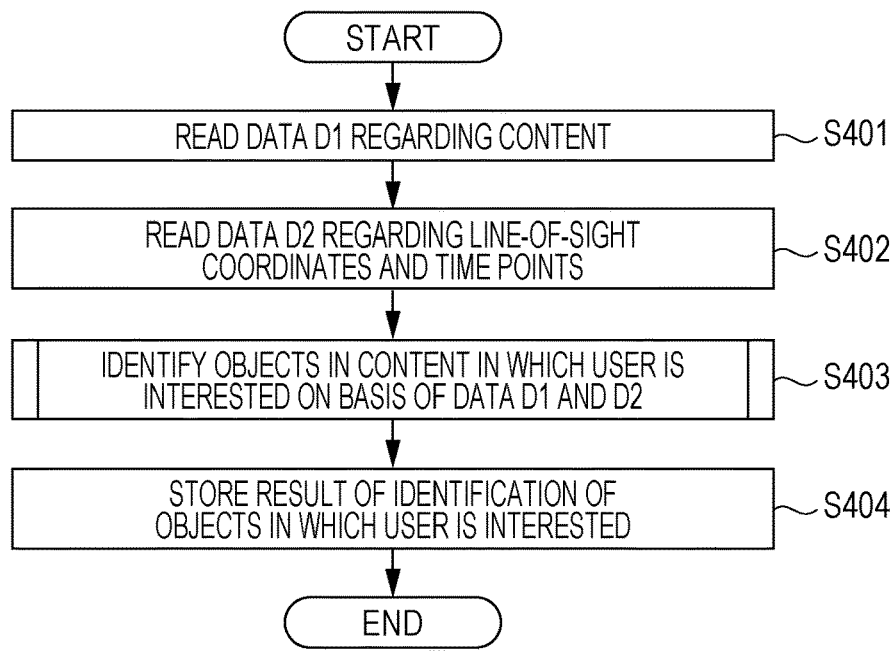
FIG. 14A is a flowchart illustrating an example of a process for identifying an object in content in which the user is interested.

FIG. 14A is a flowchart illustrating an example of a process for identifying an object in content in which the user is interested.

In step S401, the signal processing circuit 70 reads data D1 regarding content from the server 200. The data D1 is data regarding content to be presented to the user, such as a video, a sound, an application, a video game, or a task.

In step S402, the signal processing circuit 70 reads data D2 regarding line-of-sight coordinates and time points from the server 200. The data D2 is stored in advance in step S317, which has been described above.

In step S403, the signal processing circuit 70 identifies, on the basis of the data D1 and D2, one or more objects in the content in which the user is interested. Each of the one or more objects can be, for example, a certain person, an animal, a plant, a machine, a building, or a scene. Details of step S403 will be described later with reference to FIG. 14B.

In step S404, the signal processing circuit 70 stores, in the server 200, a result of the identification of one or more objects in the content in which the user is interested.

The details of step S403 will be described hereinafter.

Figure 14B:
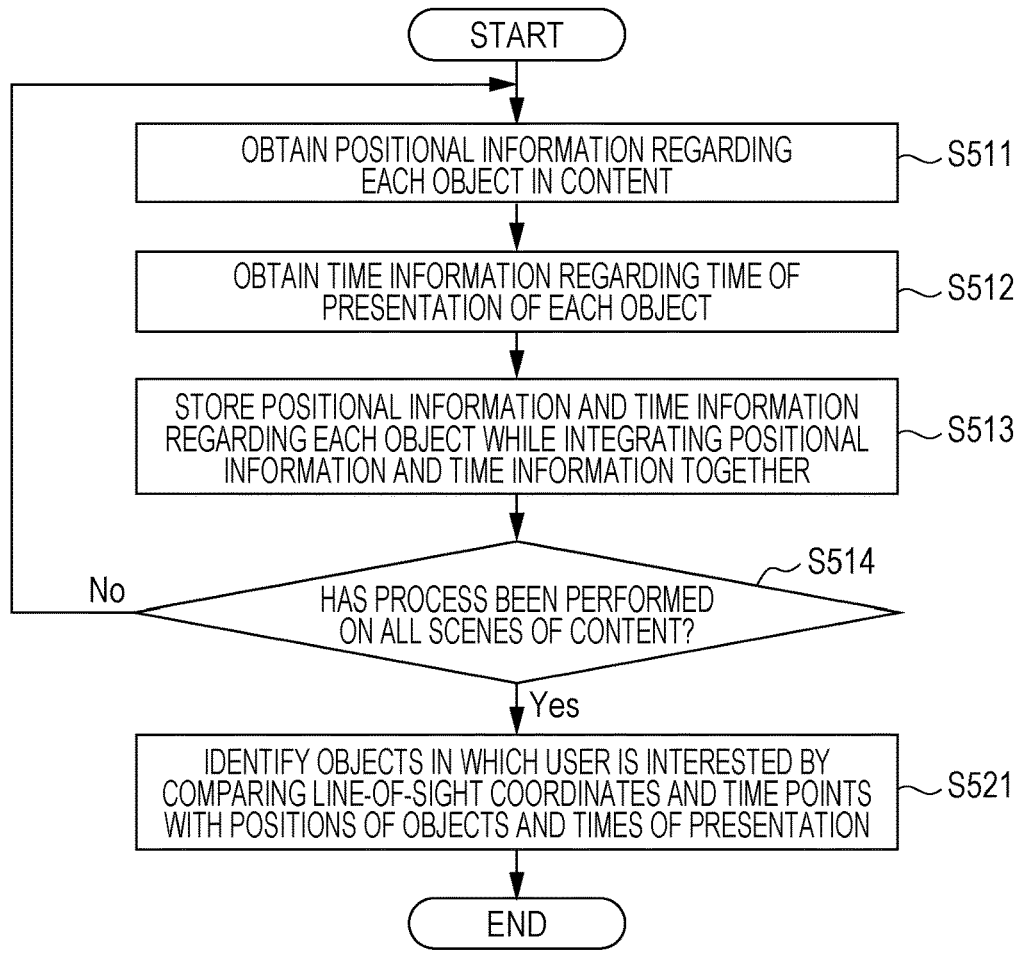
FIG. 14B is a flowchart illustrating details of step S403 illustrated in FIG. 14A.

FIG. 14B is a flowchart illustrating the details of step S403. The signal processing circuit 70 repeats steps S511 to S514 illustrated in FIG. 14B for all scenes of the content. The signal processing circuit 70 then performs step S521.

In step S511, the signal processing circuit 70 obtains positional information regarding each object in the content. Each object can be, for example, a person, an animal, a plant, or the like that appears in an application or a moving image. The positional information regarding each object may be included in the data D1 regarding the content or generated by analyzing the data D1 using the signal processing circuit 70.

In step S512, the signal processing circuit 70 obtains time information regarding a time of presentation of each object. A time of presentation indicates a timing in the content at which each object appears. The time information may be included in the data D1 in advance or generated by analyzing the data D1 using the signal processing circuit 70.

In step S513, the signal processing circuit 70 stores the positional information and the time information regarding each object in the server 200 while integrating the positional information and the time information together.

Steps S511 to S513 are repeated until it is determined in step S514 that steps S511 to S513 have been completed for all the scenes of the content. When steps S511 to S513 have been completed for all the scenes of the content, the process proceeds to step S521.

In step S521, the signal processing circuit 70 identifies one or more objects in which the user is interested by comparing the line-of-sight coordinates and the time points indicated by the data D2 with positions of the objects and the times of presentation. When the line-of-sight coordinates and position coordinates of the objects are represented in the same display coordinate system, for example, coordinates can be simply compared with each other. When step S521 ends, the process proceeds to step S404 illustrated in FIG. 14A, and a result of the identification is stored.

4-3. Second Applied Process after Determination of Degree of Interest of User

Next, an example of a process for changing content to be presented to the user in accordance with a target of interest of the user will be described.

In the present embodiment, while content such as an application or a moving image is being presented to the user, the biometric apparatus 100 begins to generate data indicating the appearance of the user's face and data indicating a state of cerebral blood flow. If a target of interest of the user is identified on the basis of the generated data, content to be presented next, such as an application or a moving image, can be appropriately changed in accordance with the target of interest. If it is found while the user is viewing a moving image for presenting a travel destination that the user is interested in places to stay, for example, the moving image may be modified in such a way as to focus on information regarding places to stay. If the user does not express any interest while viewing an application or a moving image, on the other hand, a predetermined template may be presented.

A stimulus to be given to the user can thus be controlled on the basis of moving image data indicating the appearance of the user's face and moving image data indicating a state of cerebral blood flow of the user. At this time, the stimulation control unit 63 of the control circuit 60 can cause the stimulation device 10 to output at least either a video or a sound associated with a classification of biological reaction. A classification of biological reaction can be one of two classifications such as "interested" and "not interested". Alternatively, the degree of interest or another state may be divided into three or more classifications.

Figure 15:
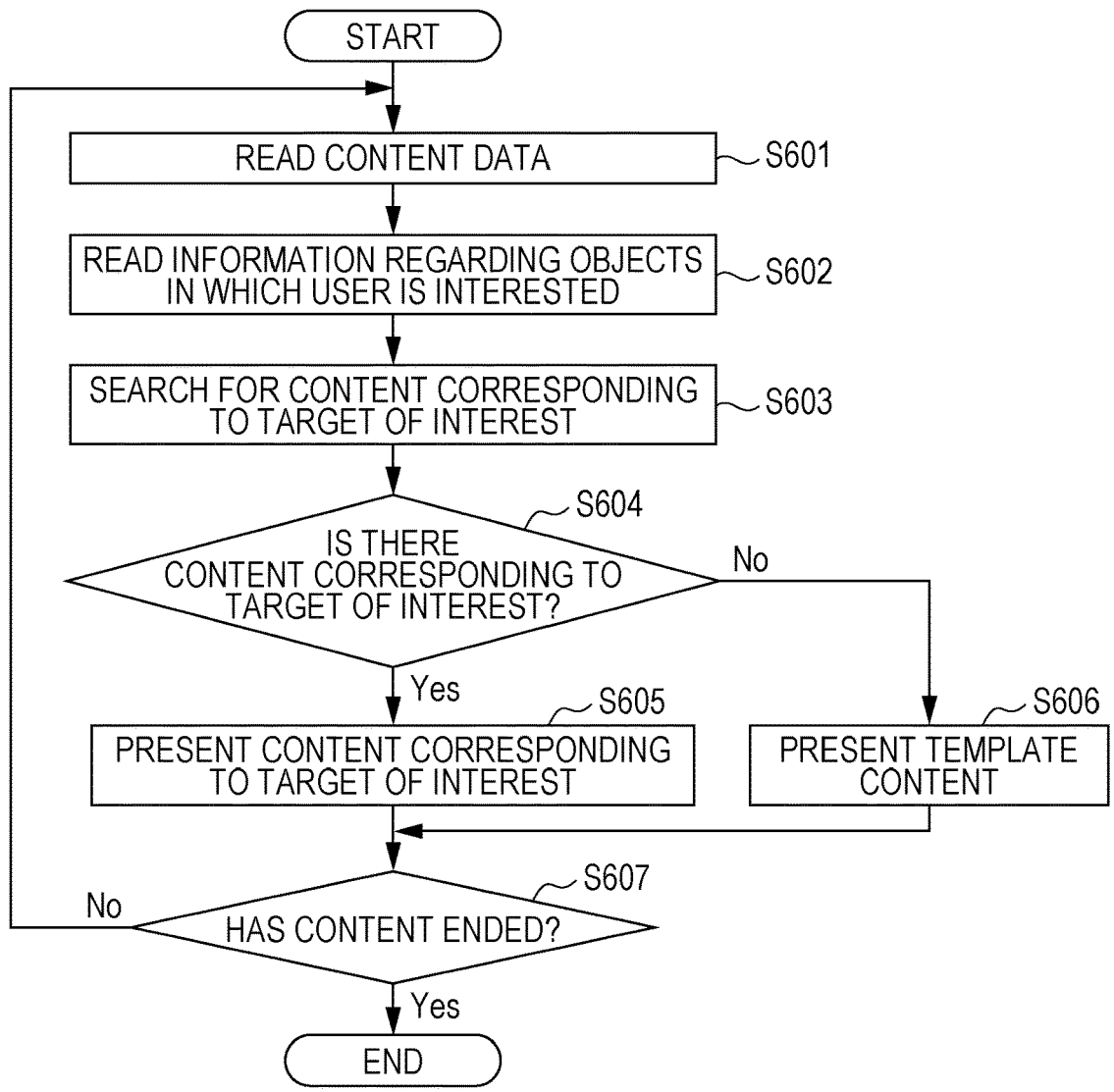
FIG. 15 is a flowchart illustrating an example of a process for changing content in accordance with a target of interest of the user.

FIG. 15 is a flowchart illustrating an example of a process for changing content in accordance with a target of interest of the user.

In step S601, the signal processing circuit 70 reads, from the server 200, information regarding content presented to the user. In step S602, the signal processing circuit 70 reads information regarding one or more objects in which the user is interested, the information having been stored in step S404 illustrated in FIG. 14A.

In step S603, the signal processing circuit 70 accesses the server 200 and searches for content corresponding to a target of interest. If it is found that the user is interested in real estate, for example, the signal processing circuit 70 searches for content including real estate information.

In step S604, the signal processing circuit 70 determines whether there is content corresponding to the target of interest of the user. If not, the process proceeds to step S606, and predetermined template content is presented. If there is content corresponding to the target of interest of the user, the process proceeds to step S605, and the content corresponding to the target of interest of the user is presented.

The above process is repeated until it is determined in step S607 that the content has ended. As a result of the above process, appropriate content corresponding to a target of interest of the user can be presented to the user.

The process illustrated in FIG. 15 may be performed after the process illustrated in FIG. 14A is completed or in parallel with the process illustrated in FIG. 14A.

Figure 16:
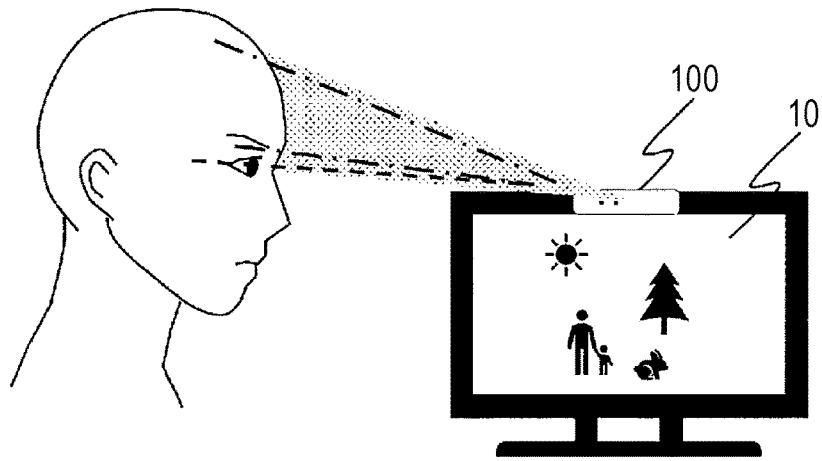
FIG. 16 is a diagram schematically illustrating an example of use of the biometric apparatus.

FIG. 16 schematically illustrates a situation where the stimulation device 10 including a display capable of connecting to a network is giving the user a moving image presented by the server 200 as a stimulus. The user is given a stimulus such as a moving image by the stimulation device 10 such as a PC or a television set. While the user is viewing the moving image, the biometric apparatus 100 incorporated into or connected to the PC or the television set obtains cerebral blood flow information and appearance information regarding the user.

Figure 17:
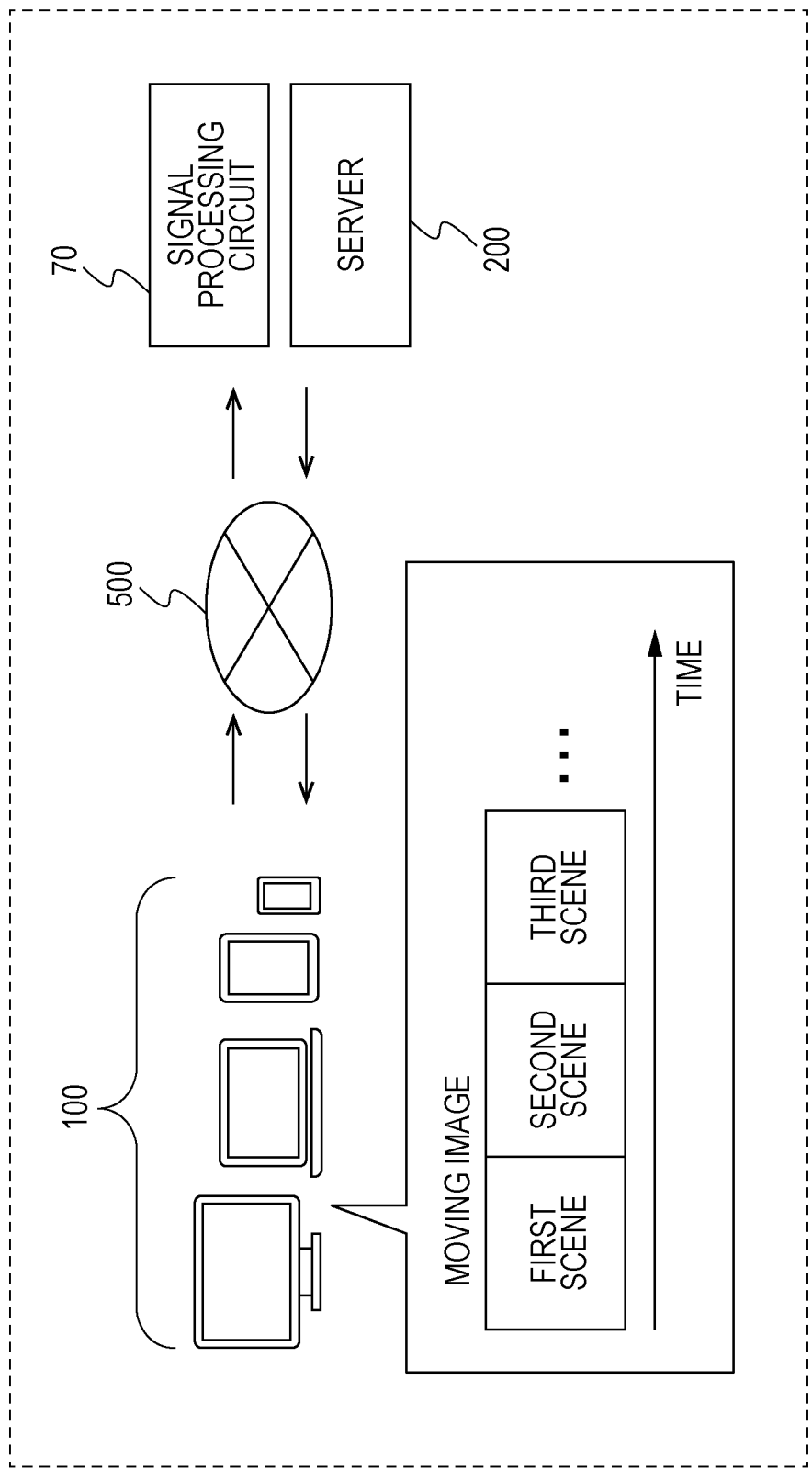
FIG. 17 is a diagram illustrating an example of a system that changes content to be presented to the user in accordance with the target of interest of the user.

FIG. 17 is a diagram illustrating an example of a system that changes content to be presented to the user in accordance with the target of interest of the user. In this example, the biometric apparatus 100 incorporated into or connected to an information device such as a PC, a television set, a tablet computer, a smartphone, or a head-mounted display, the signal processing circuit 70, and the server 200 are provided at different places and connected to one another over a network 500. As in this example, the signal processing circuit 70 illustrated in FIG. 1B may be provided outside the biometric apparatus 100.

In this example, the cerebral blood flow information and the appearance information obtained from the user using the biometric apparatus 100 are transmitted to the signal processing circuit 70 over the network 500. The signal processing circuit 70 identifies a target of interest of the user using the received information. A scene of a moving image to be presented to the user next is determined on the basis of the identified target of interest, and data indicating the scene is transmitted to the stimulation device 10 such as a display. A video stimulus presented to the user can change in real-time or at certain time intervals in accordance with the target of interest of the user. For example, the moving image includes scenes played back successively. Second and later scenes may be determined in accordance with a classification of interest of the user identified in previous scenes.

5. Other Embodiments

The above embodiment is just an example, and may be modified in various ways. Differences from the above-described examples of configuration and operation will be mainly described hereinafter, and redundant description is omitted.

5-1. Determination of Degree of Understanding Based on Pupil Diameter

For example, the pupil diameter of the user may be detected on the basis of a signal output from the image sensor 30. When the brain works hard, the autonomous nervous system increases the pupil diameter, and when the brain is at rest, the autonomous nervous system reduces the pupil diameter. Information regarding the pupil diameter of the user can be obtained by the signal processing circuit 70 capable of using a technique for recognizing the pupil. The signal processing circuit 70 can determine a degree of understanding of the user during learning on the basis of the detected pupil diameter and the information indicating changes in cerebral blood flow generated in step S204 illustrated in FIG. 12A. For example, the biometric apparatus 100 can determine whether the user is keeping up with a talk during a foreign language lesson by detecting the pupil diameter of the user and changes in cerebral blood flow. If the pupil diameter is small and no changes are detected in cerebral blood flow, the user might not understand the talk even if he/she is nodding. In this case, a system may notify a lecturer that the user does not understand the talk. Alternatively, an information transmission terminal or an artificial intelligence (AI) robot including the biometric apparatus 100 may detect a degree of understanding of the user on the basis of the pupil diameter of the user and the information regarding changes in cerebral blood flow detected from image data obtained by the image sensor 30. The techniques in the present disclosure may be applied to a human-machine interface that flexibly changes information to be presented to the user or a talk in accordance with the detected degree of understanding. If the pupil diameter of the user is large, the user might be having difficulty understanding the information or the talk. In this case, the information or the talk may be repeated or presented more slowly.

5-2. Application Example Employing Head-Mounted Display or Smartphone

The biometric apparatus 100 may be incorporated into a device such as a head-mounted display or a smartphone.

Figure 18:
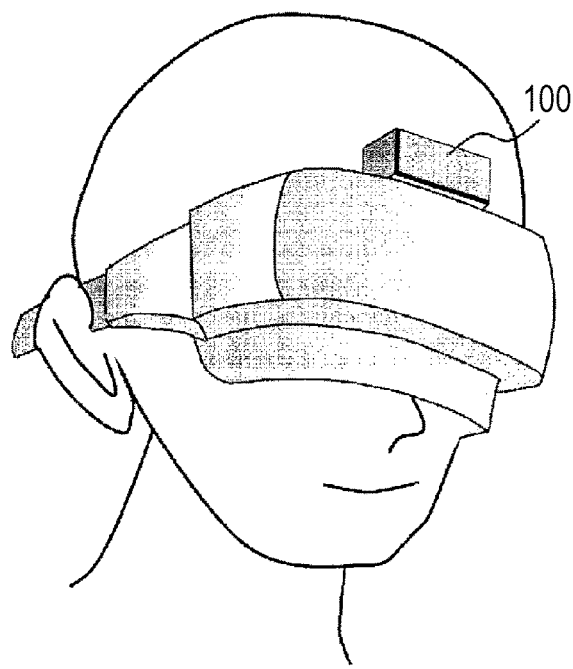
FIG. 18 is a diagram illustrating a head-mounted display including the biometric apparatus according to an embodiment.
Figure 19:
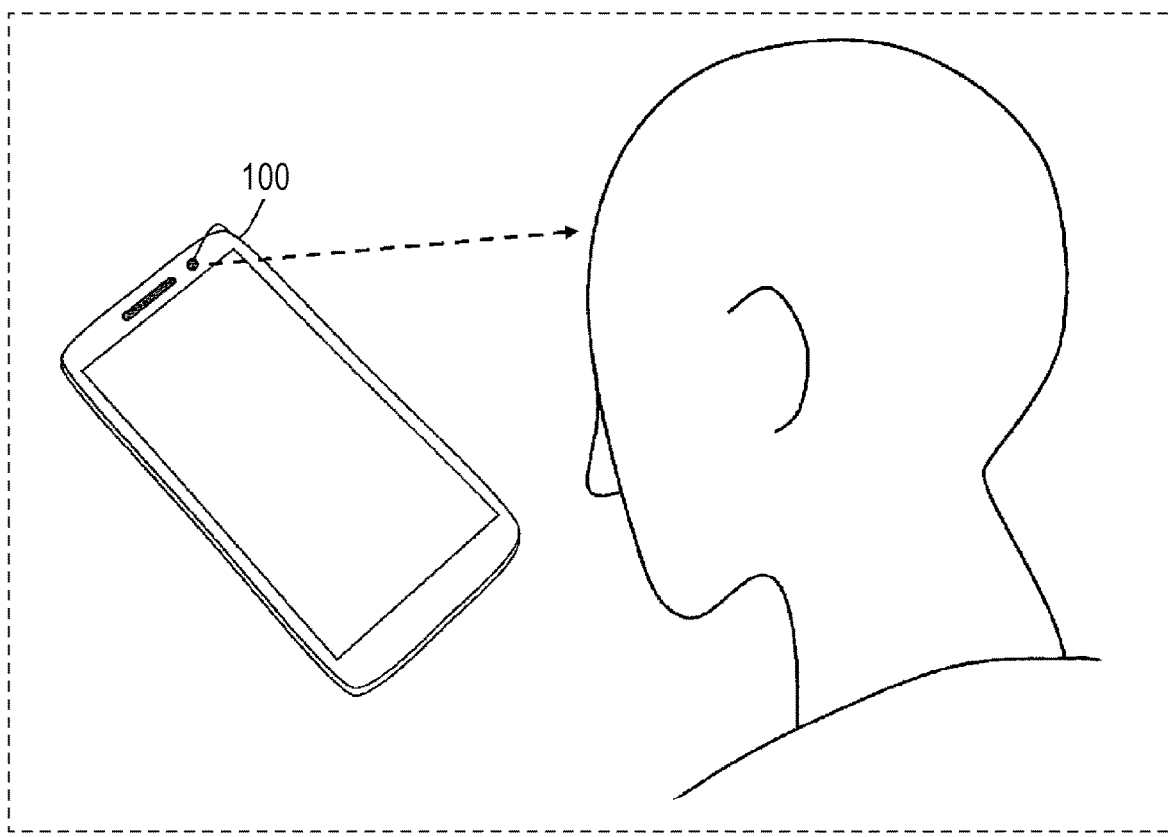
FIG. 19 is a diagram illustrating a smartphone including the biometric apparatus according to an embodiment.

FIG. 18 illustrates a head-mounted display including the biometric apparatus 100 according to an embodiment. FIG. 19 illustrates a smartphone including the biometric apparatus 100 according to an embodiment.

In the head-mounted display and the smartphone according to these embodiments, a camera incorporated into or connected to the head-mounted display or the smartphone obtains cerebral blood flow information and appearance information regarding the face. The head-mounted display and the smartphone according to the embodiments can be used in the following manner.

For example, a position on a display in which the user is interested can be identified on the basis of the line-of-sight data J1 in step S202 illustrated in FIG. 12A and the cerebral blood flow data J2 in step S204. The following operations, for example, can be performed on the basis of information regarding the identified positions.

Highlight the position on the display in which the user is interested.

Increase resolution around the position.

Display a pointer or a cursor at the position.

Identify an object in which the user is interested and display detailed information regarding the object. The object may be an actual object or a virtual object.

Feed information regarding the object in which the user is interested back to a device that has transmitted the detailed information. For example, store data indicating feedback in the server.

Store interest information in the server while associating the interest information with user information.

Turn off the smartphone or put the smartphone to sleep if the user does not look at the smartphone for a long time.

In addition, information indicating the frequency or time intervals of blinking of the user may be used as information indicating changes in the appearance of the face instead of the line-of-sight data J1 in step S202 illustrated in FIG. 12A. A degree of fatigue or concentration of the user can be estimated on the basis of the information indicating the frequency or the time intervals of blinking and the information indicating changes in cerebral blood flow. The following operations, for example, can be performed on the basis of information regarding the estimated degree of fatigue or concentration.

Display a message for encouraging a break.

Display a relaxing image.

Monitor the degree of fatigue, an operation load, operation difficulty, or a degree of proficiency of the user in an operation.

Reduce display illumination.

Monitor a degree of proficiency of the user in an application or a video game.

Turn off or on the smartphone.

In addition, the user's sleepiness can be estimated on the basis of the information regarding the frequency or the time intervals of blinking and the information regarding changes in cerebral blood flow. The following operations, for example, can be performed on the basis of information regarding the estimated sleepiness.

Turn off or on the head-mounted display.

Display a message for unauthorized refreshment.

Display an image that would awake the user.

Furthermore, a degree of interest in content or information regarding evaluation of appropriateness of illumination can be obtained on the basis of the information regarding the pupil diameter and the information regarding changes in cerebral blood flow. Depending on the degree of interest in content or the information regarding evaluation of appropriateness of illumination, whether to change content or whether to increase or reduce illumination can be determined.

In the above embodiments of the present disclosure, data indicating temporal changes in a face image and data indicating temporal changes in cerebral blood flow can be obtained. Information regarding identification or authentication of the user can also be obtained on the basis of these pieces of data. The following operations, for example, can be performed on the basis of the information regarding identification or authentication of the user.

Select content to be displayed.

Disable the apparatus for unexpected users.

Set an upper limit to use time to suppress accumulation of fatigue.

By using not only a face image but also cerebral blood flow information, impersonation using a silicone mask, which is often used in special makeup, a photograph, or a mannequin can be prevented.

5-3. Application Example for Vehicle

Figure 20:
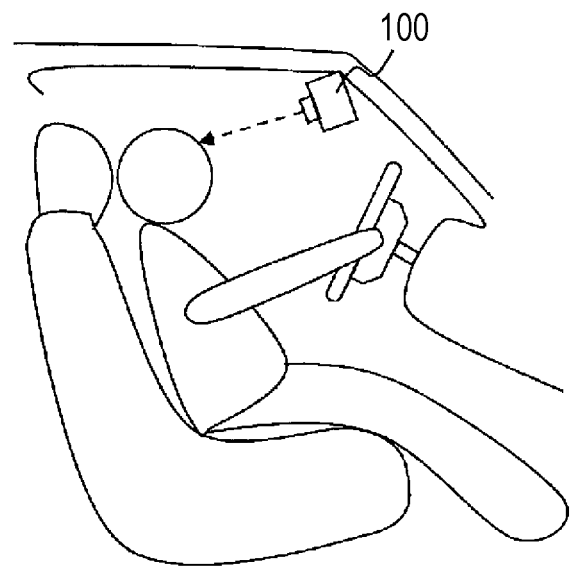
FIG. 20 is a diagram schematically illustrating a situation where the user is using the biometric apparatus mounted on a vehicle.

The biometric apparatus 100 may be mounted on a vehicle. FIG. 20 is a diagram schematically illustrating a situation where the user is using the biometric apparatus 100 mounted on a vehicle.

In this example, the biometric apparatus 100 may be incorporated into the vehicle or connected to the vehicle. The biometric apparatus 100 may be specialized in biometrics or incorporated into another device such as a driving recorder or an automotive navigation system. A stimulus may be presented to a person other than the user, instead.

When the biometric apparatus 100 is mounted on a vehicle, the biometric apparatus 100 may be used in the following manner. For example, information regarding a line of sight or blinking can be obtained as information indicating changes in the appearance of the face. Information indicating a sudden illness such as myocardial infarction or stroke or an abnormal state of consciousness such as intoxication, for example, can be obtained on the basis of the information regarding a line of sight or blinking and the information regarding changes in cerebral blood flow. The following operations, for example, can be performed on the basis of the information indicating a sudden illness or an abnormal state of consciousness.

Stop the vehicle.

Flash hazard lights or a blue lamp of a bus.

Display "Emergency" on an electric bulletin board of a bus.

Switch to self-driving and safely stop the vehicle.

Issue an audio message for encouraging a break or calling attention.

Limit maximum speed.

Disable an engine.

In this example, the stimulation device 10 can be a vehicle lamp or an electric bulletin board. In this case, a stimulus can be presented to a person other than the user.

Furthermore, information indicating interest in a gaze point can be obtained on the basis of the information regarding the pupil diameter or a line of sight and the information regarding changes in cerebral blood flow. On the basis of the information indicating interest in a gaze point, for example, detailed information regarding an object at the gaze point, that is, for example, recommended information or availability information regarding parking lots, can be displayed or a message relating to the object can be issued.

In addition, information regarding identification or authentication of the user can be obtained on the basis of information regarding changes in a face image and information regarding changes in cerebral blood flow. On the basis of the information regarding identification or authentication of the user, the apparatus may be disabled or an engine may be stopped if an unauthorized user is trying to operate.

5-4. Application Example for Caregiving or Hospital Stay

Figure 21:
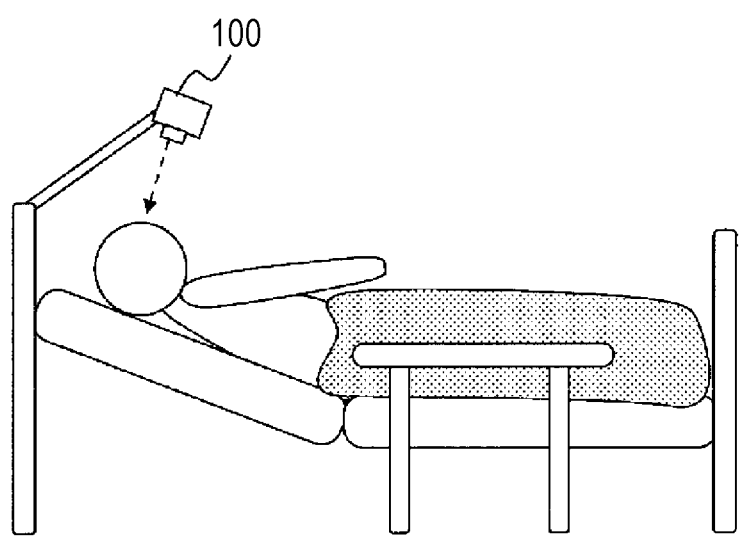
FIG. 21 is a diagram illustrating an example in which a patient is using the biometric apparatus in a bed.

Furthermore, the biometric apparatus 100 may be installed above a bed used for caregiving or hospital stay. FIG. 21 illustrates an example in which a target, that is, a patient, uses the biometric apparatus 100 in a bed.

In this example, information regarding a line of sight or facial expression of the patient can be obtained as information regarding changes in the appearance of the face. Information indicating a physical state of the patient, such as a cognitive state, pain, or a desire to urinate or defecate can be obtained on the basis of the information regarding a line of sight or facial expression and information regarding changes in cerebral blood flow. Information can be transmitted to a care worker, a nurse, or a doctor on the basis of the information indicating the physical state of the patient.

Information regarding the pupil diameter can be obtained as the information regarding changes in the appearance of the face. Information indicating a consciousness level or a vital state can be obtained on the basis of the obtained information regarding the pupil diameter and the information regarding changes in cerebral blood flow. Information can be transmitted to a care worker, a nurse, or a doctor on the basis of the information indicating a consciousness level or a vital state.

A biometric apparatus in the present disclosure can be used, for example, for various apparatuses such as cameras, measuring devices, and information devices that obtain internal information regarding users in a noncontact manner.

What is claimed is:

1. A biometric apparatus comprising:
   a light source that emits a light pulse radiated onto a target part including a head of a target;
   an image sensor that receives a reflected light pulse which is caused as the light pulse is radiated onto the target part, and that outputs first image data indicating appearance of a face of the target and second image data according to distribution of an amount of light of at least one of components of the reflected light pulse;
   a control circuit that controls the light source and the image sensor; and
   a signal processing circuit, wherein
   the control circuit causes the light source to emit the light pulse repeatedly and the image sensor to output the first image data and the second image data, and
   the signal processing circuit generates data indicating a state of the target based on a temporal change in the first image data and a temporal change in the second image data and outputs the data.

2. The biometric apparatus according to claim 1, wherein the control circuit causes the image sensor to generate the second image data by causing the image sensor to detect a component of the reflected light pulse in a period including at least a part of a falling period, the falling period being a period from a beginning to an end of a decrease in intensity of the reflected light pulse, after the falling period starts.

3. The biometric apparatus according to claim 2, wherein the control circuit causes the image sensor to generate the first image data by causing the image sensor to detect a component of the reflected light pulse in a period including at least a part of a period before the falling period of the reflected light pulse starts.

4. The biometric apparatus according to claim 1, wherein resolution of the first image data and resolution of the second image data are different from each other.

5. The biometric apparatus according to claim 1, wherein resolution of the first image data is higher than resolution of the second image data.

6. The biometric apparatus according to claim 1, wherein the signal processing circuit further performs a process for changing at least one resolution selected from the group consisting of resolution of at least a part of an image indicated by the first image data and resolution of at least a part of an image indicated by the second image data, and
the signal processing circuit generates the data indicating the state of the target based on the temporal change in the first image data and the temporal change in the second image data after the process is performed.

7. The biometric apparatus according to claim 1, wherein the image sensor outputs the first image data at a first frame rate,
the image sensor outputs the second image data at a second frame rate, and
the first frame rate and the second frame rate are different from each other.

8. The biometric apparatus according to claim 1, wherein the image sensor outputs the first image data at a first frame rate,
the image sensor outputs the second image data at a second frame rate, and
the first frame rate is higher than the second frame rate.

9. The biometric apparatus according to claim 1, wherein the image sensor includes light detection cells arranged in two dimensions,
each of the light detection cells includes a photoelectric conversion element, a first charge accumulator, and a second charge accumulator,
the control circuit causes the first charge accumulator to accumulate first charge,
the first image data is generated based on the first charge,
the control circuit causes the second charge accumulator to accumulate second charge, and
the second image data is generated based on the second charge.

10. The biometric apparatus according to claim 1, wherein the signal processing circuit detects, based on the temporal change in the first image data, a temporal change in appearance information indicating at least one selected from the group consisting of a line of sight of the target, size of a pupil of the target, frequency of blinking of the target, time intervals of blinking of the target, and facial expression of the target, and the signal processing circuit generates the data indicating the state of the target based on the temporal change in the appearance information and the temporal change in the second image data.

11. The biometric apparatus according to claim 1, wherein the control circuit causes the light source to emit the light pulse and the image sensor to generate the first image data and the second image data with a stimulus given to the target, and the data indicating the state of the target indicates at least one state selected from the group consisting of interest of the target, comfort of the target, sleepiness of the target, and concentration of the target in reaction to the stimulus.

12. The biometric apparatus according to claim 1, wherein the signal processing circuit presents the data indicating the state of the target to the target through an information device.

13. The biometric apparatus according to claim 1, wherein the biometric apparatus controls the vehicle based on the data.

14. The biometric apparatus according to claim 13, wherein the biometric apparatus causes the vehicle to flash hazard lights of the vehicle after the biometric apparatus confirms the data indicating an abnormal state of consciousness.

15. The biometric apparatus according to claim 13, wherein the biometric apparatus causes the vehicle to limit maximum speed of the vehicle after the biometric apparatus confirms the data indicating an abnormal state of consciousness.

16. The biometric apparatus according to claim 13, wherein the biometric apparatus causes the vehicle to disable an engine of the vehicle after the biometric apparatus confirms the data indicating an abnormal state of consciousness.

17. A biometric method comprising:

causing a light source to repeatedly emit a light pulse radiated onto a target part including a head of a target;

causing an image sensor to receive a reflected light pulse which is caused as the light pulse is radiated onto the target part;

causing the image sensor to output first image data indicating appearance of a face of the target;

causing the image sensor to output second image data according to distribution of an amount of light of at least one of components of the reflected light pulse; and generating data indicating a state of the target based on a temporal change in the first image data and a temporal change in the second image data and outputting the data.

18. A non-transitory computer-readable storage medium storing a program for measuring a state of a target, the program, when executed by a computer, causing the computer to perform a process comprising:

causing a light source to repeatedly emit a light pulse radiated onto a target part including a head of the target;

causing an image sensor to receive a reflected light pulse which is caused as the light pulse is radiated onto the target part;

causing the image sensor to output first image data indicating appearance of a face of the target;

causing the image sensor to output second image data according to distribution of an amount of light of at least one of components of the reflected light pulse; and generating data indicating the state of the target based on a temporal change in the first image data and a temporal change in the second image data and outputting the data.

* * * * *